US011007221B2

(12) United States Patent
Scott et al.

(10) Patent No.: US 11,007,221 B2
(45) Date of Patent: *May 18, 2021

(54) ACELLULAR PRO-INFLAMMATORY COMPOSITIONS, PROCESS FOR MAKING SAME AND METHODS OF USING SAME

(71) Applicant: CANADIAN BLOOD SERVICES, Ottawa (CA)

(72) Inventors: Mark D. Scott, Surrey (CA); Duncheng Wang, Greenville, NC (US); Wendy M. Toyofuku, Surrey (CA)

(73) Assignee: CANADIAN BLOOD SERVICES, Ottawa (CA)

(*) Notice: Subject to any disclaimer, the term of this patent is extended or adjusted under 35 U.S.C. 154(b) by 178 days.

This patent is subject to a terminal disclaimer.

(21) Appl. No.: 14/904,347

(22) PCT Filed: Dec. 13, 2013

(86) PCT No.: PCT/CA2013/050963
§ 371 (c)(1),
(2) Date: Jan. 11, 2016

(87) PCT Pub. No.: WO2015/003240
PCT Pub. Date: Jan. 15, 2015

(65) Prior Publication Data
US 2016/0206655 A1  Jul. 21, 2016

Related U.S. Application Data

(63) Continuation of application No. PCT/CA2013/050546, filed on Jul. 12, 2013, and a continuation of application No. PCT/CA2013/050543, filed on Jul. 12, 2013.

(51) Int. Cl.
*C12N 15/11* (2006.01)
*A61K 35/17* (2015.01)
*A61K 31/7105* (2006.01)
*A61K 35/15* (2015.01)
*A61K 35/26* (2015.01)
*C12N 5/0783* (2010.01)
*C12N 5/078* (2010.01)
*C12N 15/113* (2010.01)

(52) U.S. Cl.
CPC .......... *A61K 35/17* (2013.01); *A61K 31/7105* (2013.01); *A61K 35/15* (2013.01); *A61K 35/26* (2013.01); *C12N 5/0636* (2013.01); *C12N 5/0648* (2013.01); *C12N 15/111* (2013.01); *C12N 15/113* (2013.01); *C12N 2310/141* (2013.01); *C12N 2320/30* (2013.01); *C12N 2500/50* (2013.01); *C12N 2502/1114* (2013.01); *C12N 2502/1178* (2013.01)

(58) Field of Classification Search
None
See application file for complete search history.

(56) References Cited

U.S. PATENT DOCUMENTS

| 5,908,624 | A | 6/1999 | Scott et al. ............ 424/93.7 |
|---|---|---|---|
| 8,007,784 | B1 | 8/2011 | Scott et al. ............ 424/93.7 |
| 8,067,151 | B2 | 11/2011 | Maurer et al. ............ 435/2 |
| 2003/0091541 | A1 | 5/2003 | Ikehara et al. ............ 424/93.7 |
| 2004/0228848 | A1 | 11/2004 | Har-Noy |
| 2005/0196386 | A1 | 9/2005 | Blazar et al. ............ 424/93.7 |
| 2006/0062763 | A1 | 3/2006 | Godfrey et al. |
| 2007/0009497 | A1 | 1/2007 | Steinman et al. ......... 424/93.21 |
| 2012/0093936 | A1 | 4/2012 | Lindenberg et al. ......... 424/491 |
| 2014/0017218 | A1 | 1/2014 | Scott et al. |
| 2014/0314866 | A1 | 10/2014 | Brusko et al. ............ 424/501 |
| 2015/0164948 | A1* | 6/2015 | Scott ..................... A61K 35/17 424/93.71 |

FOREIGN PATENT DOCUMENTS

| WO | WO 97/28254 | 8/1997 |
|---|---|---|
| WO | WO 9742324 | 11/1997 |
| WO | WO 02/072799 | 9/2002 |
| WO | WO 2007120128 | 10/2007 |
| WO | WO 2009/106477 | 9/2009 |
| WO | WO 2011053223 | 5/2011 |
| WO | WO 2012/065027 | 5/2012 |
| WO | WO 2014/008608 | 1/2014 |
| WO | WO 2015/003240 | 1/2015 |

OTHER PUBLICATIONS

Turnchinovich et al., 2011, Nuc. Acid. Res. vol. 39: 7223-7233.*
Wei et al., 2012, Am. J. Transpl vol. 12: 1113-1123.*
Campo et al., 2001, Blol. Trace Elem. Res. vol. 78: 15-22.*
MirVana miRNA isolation kit, 2011, pp. 1-29.*
Kang et al., 2017, Acta Biomat. vol. 578: 146-155.*
Mittelbrunn eta l., 2011, Nat. comm. vol. 2: 1-10.*
Kosaka et al., 2010, J. Biol. Chem. vol. 285: 17442-17452.*
Anderson MS, Bluestone JA. "The NOD mouse: a model of immune dysregulation." *Annu Rev Immunol*. 2005;23:447-85.
Bradley and Scott, "Immune complex binding by immunocamouflaged [poly(ethylene glycol)-grafted]erythrocytes", *Am J Hematol*, 82:970-975, 2007.
Bradley et al. Separation and purification of methoxypoly(ethylene glycol) grafted red blood cells via two-phase partitioning.*J Chromatogr B Analyt Technol Biomed Life Sci.*, 807(1):163-8, 2004.

(Continued)

*Primary Examiner* — Amy E Juedes
(74) *Attorney, Agent, or Firm* — Norton Rose Fulbright US LLP

(57) ABSTRACT

This invention relates to acellular-based therapies for decreasing the level of regulatory T cells (Treg) and/or increasing the level of pro-inflammatory T cells (Th17) to favor immune stimulation. To provide these therapeutic effects, an allogeneic leukocyte population is contacted with another leukocyte population and the acellular components produced are isolated. The leukocyte populations are contacted so as to allow pro-inflammatory allo-recognition. Acellular-based preparations and processes for achieving therapy are also provided.

18 Claims, 19 Drawing Sheets

(56) References Cited

OTHER PUBLICATIONS

Bradley et al., "Interactions of IgM Abo antibodies and complement with methoxy-PEG-modified human RBCs", *Transfusion*, 41:1225-1233,2001.

Burrell et al. "Regulatory T Cell Induction, Migration, and Function in Transplantation" *J. Immunol*, 189:4705-4711,2012.

Chen and Scott, "Current and future applications of immunological attenuation via pegylation of cells and tissue", *BioDrug*, 15:833-847,2001.

Dai et al., "MicroRNA, a new paradigm for understanding immunoregulation, inflammation, and autoimmune diseases," *Translational Research*, 157(4): 163-179, 2011.

Dutheil et al., "Polyethylene glycols interact with membrane glycerophospholipids: is this part of their mechanism for hypothermic graft protection?" *J. Chem. Biol.* Mar. 2009; 2(1): 39-49.

Extended European Search Report issued in European Application No. 13816754.9, dated Mar. 4, 2016.

Extended European Search Report issued in European Application No. 13817560.9, dated Mar. 11, 2016.

Extended European Search Report issued in European Application No. 13817292.9, dated Mar. 16, 2016.

Forman et al., *The Journal of Experimental Medicine* 138:672-685, 1973.

Getts et al., "Current landscape for T-cell targeting in autoimmunity and transplantation," *Immunotherapy* 3(7): 853-870, 2011.

Hardy et al., *Nature* 223: 511-512, 1969.

Harris et al., "MicroRNAs as Immune Regulators: Implications for Transplantation," *American Journal of Transplantation*, 10(4): 713-719, 2010.

Le and Scott, "Immunocamouflage: The biophysical basis of immunoprotection by grafted methoxypoly(ethylene glycol) (mPEG)", *Acta Biomater*, 6:2631-2641, 2010.

McCoy and Scott, "Broad-Spectrum Antiviral Prophylaxis: Inhibition of Viral Infection by Polymer Grafting with Methoxypoly (ethylene glycol)", In: *Antiviral drug discovery for emerging diseases and bioterrorism threats.*, PF T, editor, Hoboken, NJ: Wiley & Sons; p. 379-395, 2005.

Miroux et al. "In Vitro Effects of Cyclosporine A and Tacrolimus on Regulatory T-Cell Proliferation and Function" *Transplantation*, 94(2): 123-31,2012.

Morita et al., *Proc. Natl. Acad. Sci.* USA 95:6947-6952, 1998.

Murad et al., "Structural and Functional consequences of Antigenic Modulation of Red Blood Cells With Methoxypoly(Ethylene Glycol)", *Blood*, 93:2121-2127, 1999.

Scott et al. "Beyond the red cell: pegylation of other blood cells and tissues" *Transfus Clin Biol.*, 11(1):40-6, 2004.

Scott et al. "Stealth erythrocytes: effects of polymer grafting on biophysical, biological and immunological parameters" *Blood Transfusion*, 1: 244-65, 2003.

Scott et al., "Chemical camouflage of antigenic determinants: Stealth erythrocytes", *Proc. Natl. Acad. Sci. USA*, 94:7566-7571, 1997.

Spiegel et al., "Role of microRNAs in immunity and organ transplantation," *Expert Reviews in Molecular Medicine*, 13: e37, 2011.

Sutton and Scott, "The effect of grafted methoxypoly(ethylene glycol) chain length on the inhibition of respiratory syncytial virus (RSV) infection and proliferation", *Biomaterials*, 31 :4223-4230, 2010.

Viegas, et al. "Polyoxazoline: chemistry, properties, and applications in drug delivery." *Bioconjugate Chemistry*. May 18, 2011 (May 18, 20 II). vol. 22, pp. 976-986. ISSN : 1043-1802.

Wang et al., "The potential utility of methoxypoly (ethylene glycol)—medicated prevention of rhesus blood group antigen RhD recognition in transfusion medicine" *Biomaterials*, 33(10): 3002-12,2012.

Wang et al., "Use of Flow Cytometry in the In Vitro and In Vivo Analysis of Tolerance/Anergy Induction by Immunocamouflage, in "Flow Cytometry—Recent Perspectives, Jun. 13, 2012, In Tech.

Yoshimura et al., *Transplantation* 49(1): 167-171, 1990.

Chen AM, Scott MD. "Comparative analysis of polymer and linker chemistries on the efficacy of immunocamouflage of murine leukocytes". *Artif Cells Blood Substit Immobil Biotechnol* 2006; 34:305-22.

Chen AM, Scott MD. "Immunocamouflage: prevention of transfusion-induced graft-versus-host disease via polymer grafting of donor cells". *J Biomed Mater Res A* 2003;67:626-36.

Murad KL, Gosselin EJ, Eaton JW, Scott MD. "Stealth cells: prevention of major histocompatibility complex class II-mediated T-cell activation by cell surface modification". *Blood* 1999;94:2135-41.

O'Connell, RM et al., "MicroRNA—155 promotes autoimmune inflammation by enhancing inflammatory T cell development", *Immunicty*, vol. 33, pp. 607-619, Oct. 29, 2010 (Oct. 29, 2010, ISSN : 1074-7613.

O'Neill DW, Bhardwaj N. "Differentiation of peripheral blood monocytes into dendritic cells". *Curr Protoc Immunol*; 2005. Chapter 22: Unit 22F.4.

Scott MD, Murad KL, Koumpouras F, Talbot M, Eaton JW. "Chemical camouflage of antigenic determinants: stealth erythrocytes". *Proc Natl Acad Sci U S A* 1997; 94:7566-71.

Stahl, HF et al., "miR-155 inhibition sensitizes CD4+ Th cells for TREG mediated suppression", vol. 4, p. e7158, *PLoS One*, Sep. 24, 2009, (Sep. 24, 2009), ISSN: 1932-6203.

Wang, D et al., "Induction of immunotolerance via mPEG grafting to allogeneic leukocytes", *Biomaterials*, vol. 32, pp. 9494-9503, Dec. 2011 (Dec. 2011), ISSN: 0142-9612.

Supplementary European Search Report issued in Application No. 13889025, dated Feb. 10, 2017.

Article 94(3) Communication issued in Application No. 13817560, dated Feb. 22, 2017.

Office Action issued in European Application No. 15818906.8, dated Nov. 7, 2017.

"MS the Disease." *National Multiple Sclerosis Society*, Aug. 4, 2015, http://www.nationalmssociety.org/About-the-Society/Press-Room/MS-the-Disease.

Combe et al., "Interleukin-2 in rheumatoid arthritis: production of and response to interleukin-2 in rheumatoid synovial fluid, synovial tissue and peripheral blood" *Clin. Exp. Immunol.* 1985, 59, 520-528.

Extended European Search Report and Opinion for EP 13817038.6, dated Feb. 12, 2016.

Extended European Search Report issued in Application No. 13817327.3, dated Mar. 11, 2016.

Kaplan, "Role of neutrophils in systemic autoimmune diseases" *Arth. Res. Ther.* 2013, 15(219):1-9.

Ling et al., "Principles of microRNA involvement in human cancers" *CACA* 2011, 30, 739-748.

*Progress in Autoimmune Diseases Research.* National Institutes of Health The Autoimmune Diseases Coordinating Committee, 2005.

Quinn et al., "How do you diagnose rheumatoid arthritis early?" *Best. Pract. Res. Clin. Rheum.* 2001, 15, 49-66.

Scott et al., "Cellular Camouflage: Fooling the Immune System with Polymers" *Current PHarm. Design* 1998, 4:423-438.

Su et al., "A simple and effective method for cancer immunotherapy by inactivated allogeneic leukocytes infusion" *Int. J. Cancer. 2009*, 124: 1142-1151.

\* cited by examiner

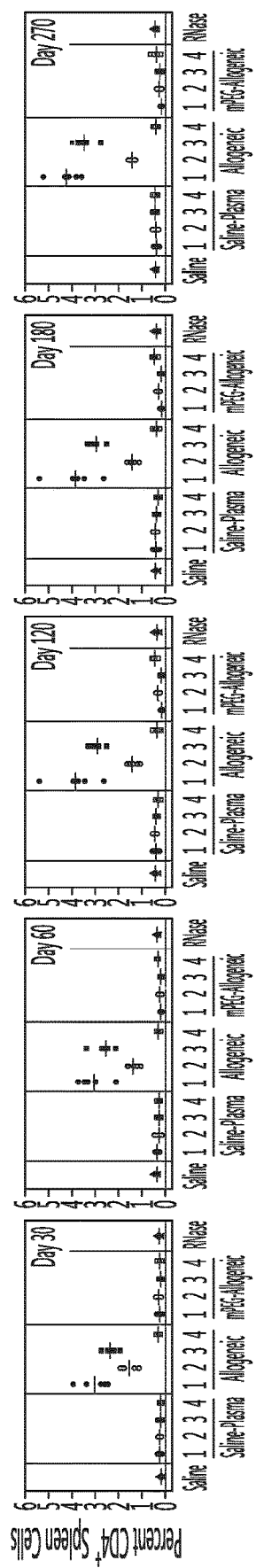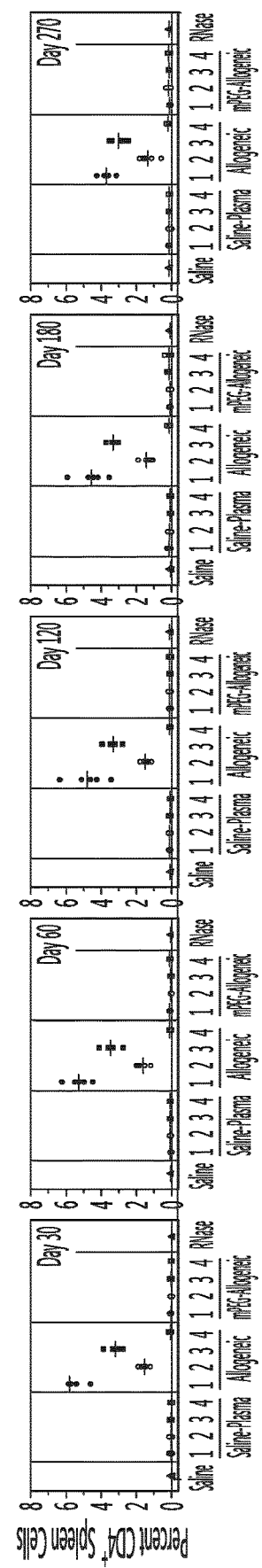
FIG. 4A
FIG. 4B

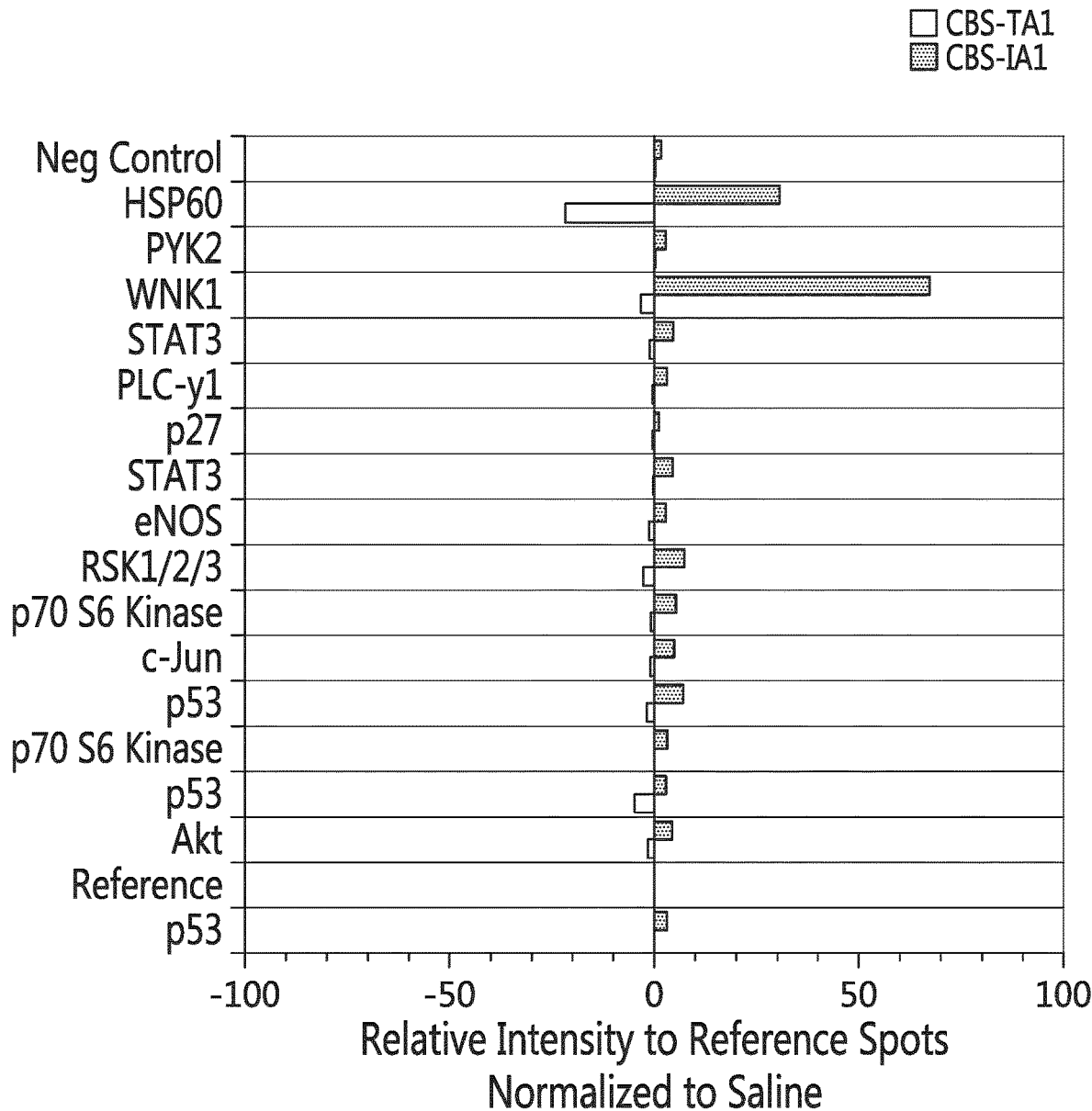

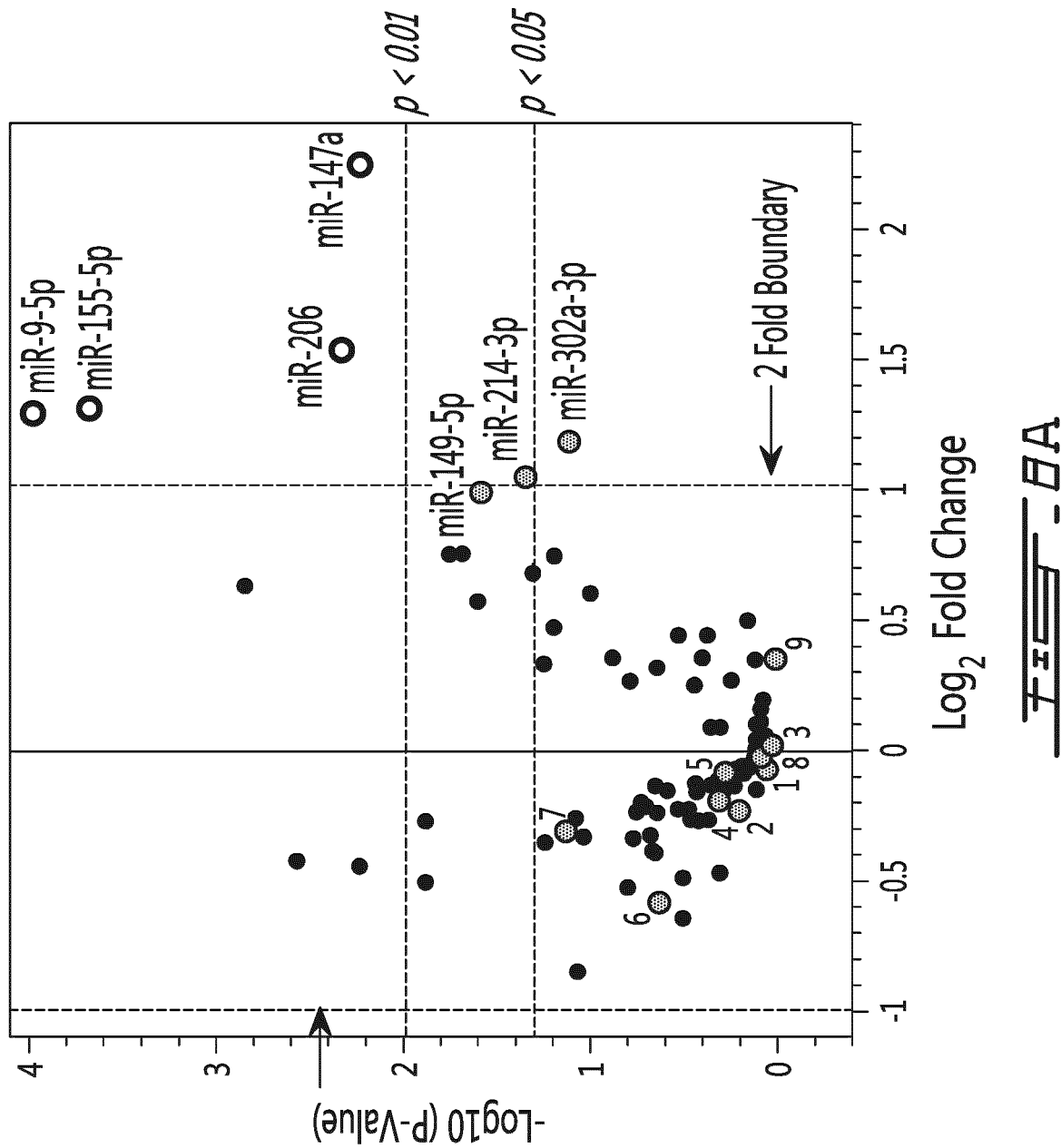

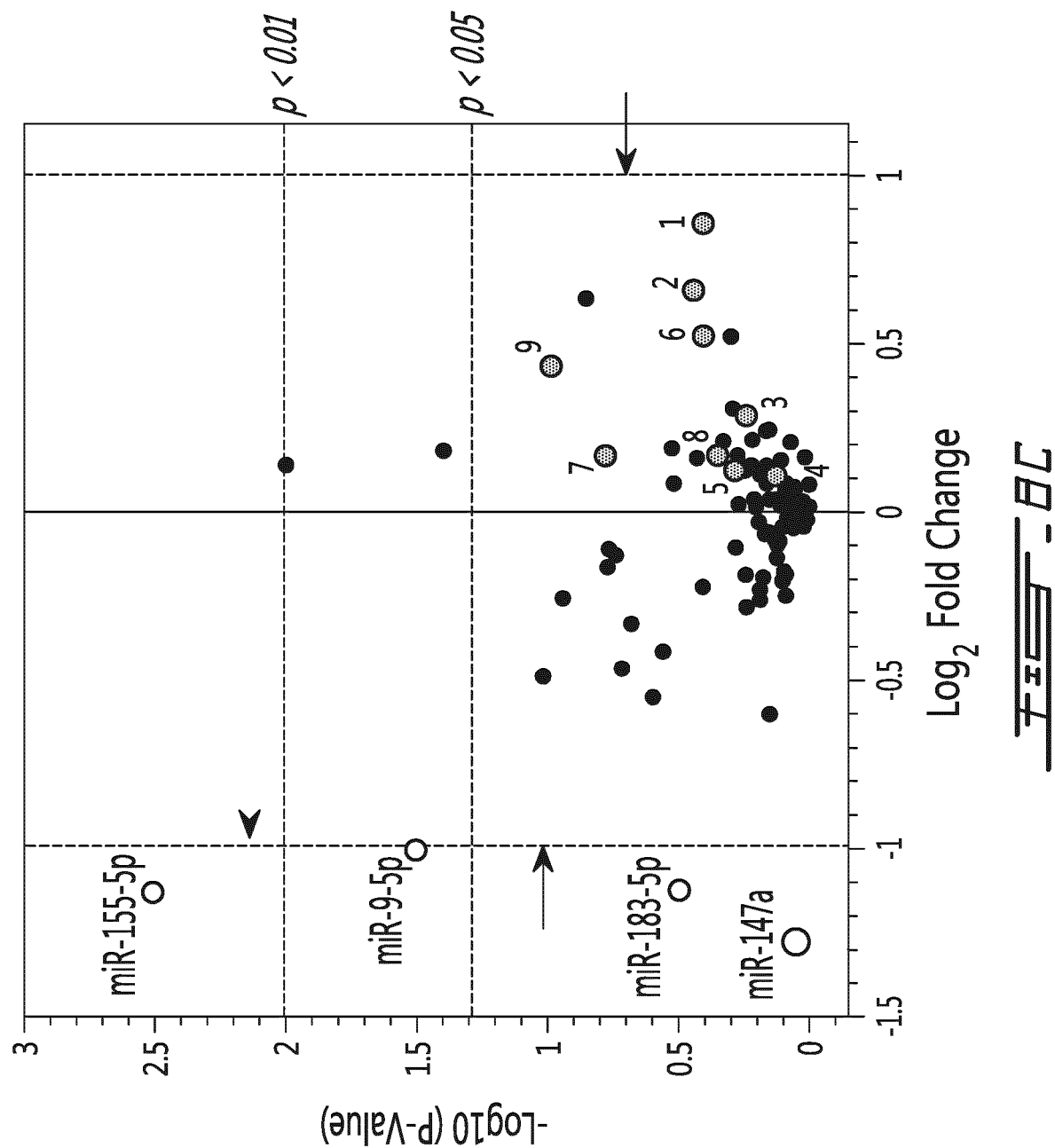

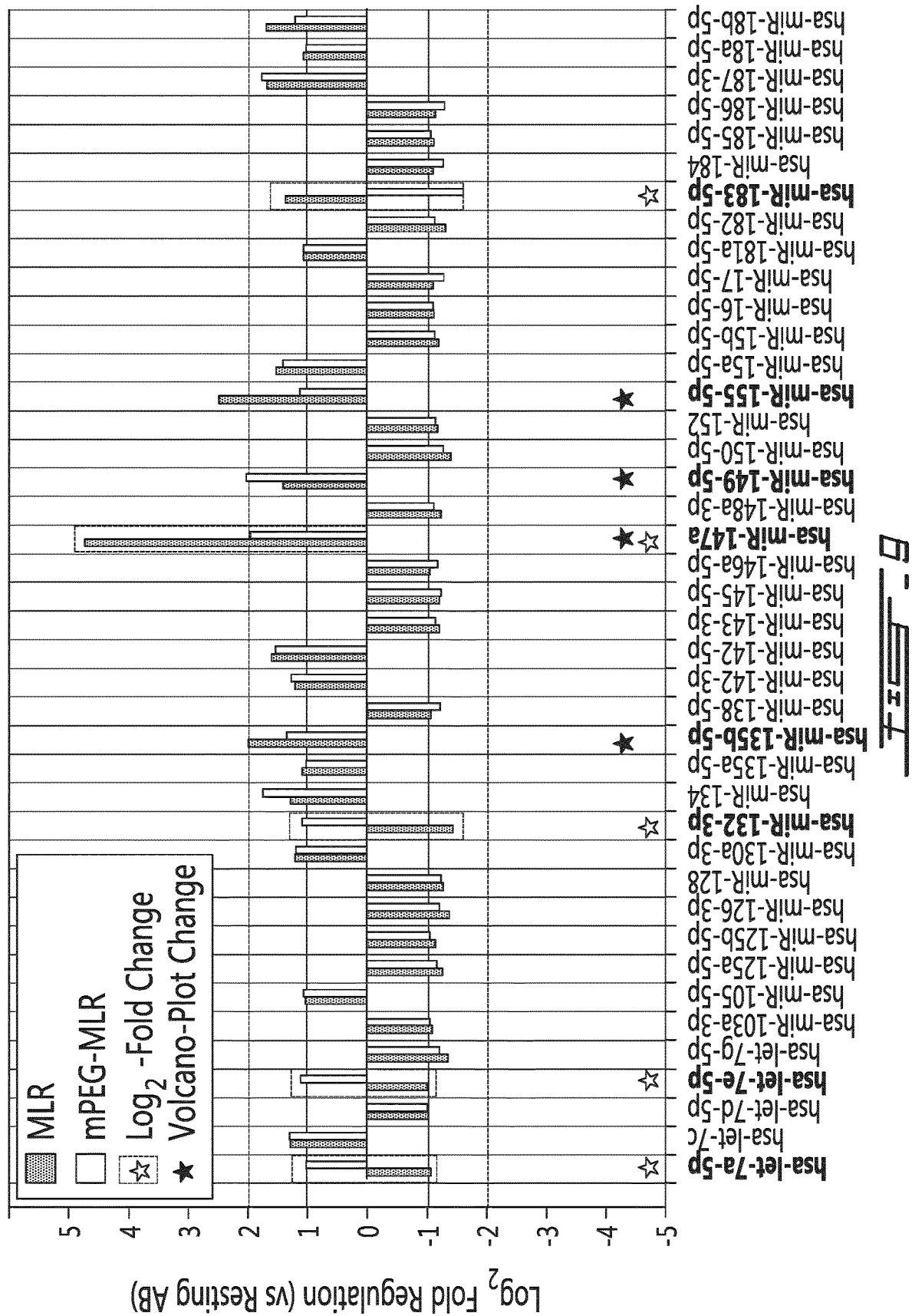

FIG. 9 CONTINUED

ACELLULAR PRO-INFLAMMATORY COMPOSITIONS, PROCESS FOR MAKING SAME AND METHODS OF USING SAME

CROSS-REFERENCE TO RELATED APPLICATIONS

This application is a national phase application under 35 U.S.C. § 371 of International Application No. PCT/CA2013/050963 filed Dec. 13, 2013, which claims priority from PCT patent applications PCT/CA2013/050546 and PCT/CA2013/050543 both filed Jul. 12, 2013. The content of these applications is incorporated herein in their entirety.

TECHNOLOGICAL FIELD

This invention relates to the use of acellular-based preparations using allogeneic leukocytes to decrease the level of regulatory T (Treg) cells and/or increase the level of pro-inflammatory T cells for inducing of an immune stimulation or a pro-inflammatory state in the treated subject. These acellular-based preparations are useful for the treatment of various conditions associated with decreased or inappropriate immune responses, such as proliferation-associated diseases and infections.

BACKGROUND

Failure of an animal's immune system to recognize and destroy abnormal cells arising from normal progenitor cells can result in uncontrolled growth and formation of tissue masses that may cause significant morbidity and mortality in the absence of ineffective therapeutic interventions. This is commonly exemplified, but not limited to, cancer cells caused by spontaneous genetic mutation and deletions or exposure to environmental agents leading to similar genetic and cellular changes. Currently, most therapeutic drugs consist of chemical cytotoxic agents targeting proliferating cells, of which the cancer cells are preferentially affected due to their higher mitotic rate, but with limited direct specificity towards the cancer cells.

New approaches attempt to overcome the lack of specificity of cytotoxic drugs by inducing (in vivo or ex vivo) a target cell antigen-specific response by clonal expansion of a subset of reactive leukocytes from the affected individual or animal. This can be done by isolating either the "target cell" (e.g. cancer cell) itself or by molecular mimicking of a target cell antigen. However, this approach is expensive and may or may not effectively stimulate the desired pro-inflammatory state in vivo. Moreover, in some cases, infective agents (e.g. viruses and parasites) may be established and persist in a subject due to a failure of the subjects immune system to effectively respond to the infective agent/organism via a pro-inflammatory mechanism. Indeed, in many cases the infective organism may actively exert an anergic effect yielding a decreased ratio of Treg to pro-inflammatory cells.

It would be highly desirable to be provided with an acellular-based preparation capable of inducing a state of immune stimulation by decreasing the ratio of the level of regulatory T cells (such as Treg) to pro-inflammatory T cells (such as Th1 and Th17). The acellular-based preparation could induce an immune stimulation either by decreasing Treg levels, increasing pro-inflammatory T cell levels or both. These preparations could be useful for treating, preventing and/or alleviating the symptoms associated to a condition associated with a low or inappropriate immune response (e.g. anergy or tolerance for example), such as a proliferation-associated disorder (cancer for example) or an infection (a parasitic infection for example).

BRIEF SUMMARY

One aim of the present invention is to provide acellular-based preparations capable of inducing a state of immune stimulation by decreasing the ratio of the level of regulatory T cells (such as Treg) to the level of pro-inflammatory T cells (such as Th1 and Th17). The acellular-based preparations could induce immune stimulation either by decreasing Treg levels, increasing pro-inflammatory T cell levels or both. These acellular-based preparations can be useful for treating, preventing and/or alleviating the symptoms associated to a condition caused/exacerbated by a low or inappropriate immune response. The acellular-based preparations and therapies presented herewith are derived from the contact of at least two distinct leukocyte populations which are considered allogeneic with respect to one another. The two leukocyte populations are contacted under conditions so as to allow pro-inflammatory allo-recognition and ultimately immune stimulation. The two leukocyte populations can be contacted in vitro, ex vivo or in vivo to induce immune stimulation and/or a pro-inflammatory state. The acellular-based preparations are obtained in a process which limits or inhibits the degradation of nucleic acids, such as miRNAs and can even include an mi-RNA enrichment step.

According to a first aspect, the present invention provides a process for making an acellular pro-inflammatory preparation. Broadly, the process comprises (i) contacting a first leukocyte with a second leukocyte under conditions to allow a pro-inflammatory allo-recognition to provide a conditioned preparation, wherein the first leukocyte is allogeneic to the second leukocyte; (ii) removing the first leukocyte and the second leukocyte from the conditioned preparation under conditions to inhibit RNA degradation so as to obtain a composition enriched in acellular pro-inflammatory components; and (iii) formulating the composition of step (ii), under conditions to inhibit RNA degradation, in the acellular pro-inflammatory preparation for administration to a subject. In an embodiment, step (i) further comprises associating a low-immunogenic biocompatible polymer to a cytoplasmic membrane of the first leukocyte. In still another embodiment, the process further comprises covalently binding the low-immunogenic biocompatible polymer to a membrane-associated protein of the cytoplasmic membrane of at least one of the first leukocyte or the second leukocyte. In still a further embodiment, the low-immunogenic biocompatible polymer is a polyethylene glycol (PEG), for example a methoxy polyethylene glycol (mPEG). In yet a further embodiment, the process further comprises covalently binding the mPEG by contacting the first leukocyte and/or the second leukocyte with methoxypoly(-ethylene glycol) succinimidyl valerate. In another embodiment, step (i) can occur in vitro, for example by culturing the first leukocyte and the second leukocyte and obtaining a supernatant of a cell culture as the conditioned preparation. In yet another embodiment, the process can further comprises, prior to step (i), preventing one of the first leukocyte or the second leukocyte from proliferating. In yet a further embodiment, step (ii) can occur in vivo and, for example, can comprise administering the first leukocyte to a mammal having the second leukocyte so as to obtain as the conditioned preparation plasma. In still a further embodiment, the process can further comprise preventing the first leukocyte from proliferating prior to administration to the mammal. In yet a further embodiment, step (ii) further comprises removing components having an average molecular weight of more than about 20 kDa or about 10 kDa from the conditioned preparation, for example by filtering out components having the average molecular weight of more than about 20 kDa or about 10 kDa from the conditioned preparation. In still another embodiment, step (ii) can further comprise enriching the conditioned preparation in at least one miRNA species. In yet another embodiment, step (iii) can further comprise formulating the composition for intravenous administration to the subject. In still a further embodiment, at least one of the first leukocyte and the second leukocyte is a T cell (such as, for example, a CD4-positive T cell or a CD8-positive T cell), a peripheral blood mononucleated cell (e.g., PBMC) or a splenocyte.

According to a second aspect, the present invention provides a pro-inflammatory preparation obtained by the process described herein. In an embodiment, the pro-inflammatory preparation has at least one, five, ten or more miRNA species presented in FIG. 9. In another embodiment, the pro-inflammatory preparation has at least one, five, ten or more of the miRNA species listed any one of Tables 1A to 1D. In still another embodiment, the pro-tolerogenic preparation has at least one, five, ten or more of the miRNA species listed in any one of Tables 2A to 2D. In yet another embodiment, the pro-tolerogenic preparation of has at least one, five, ten or more of the miRNA species identified in any one of FIGS. 8A to 8C.

According to a third aspect, the present invention provides a method of decreasing a ratio of the level of regulatory T (Treg) cells to the level of pro-inflammatory T cells in a subject in need thereof. Broadly, the method comprises administering to the subject a therapeutic amount of a pro-inflammatory preparation obtained by a process comprising: (i) contacting a first leukocyte with a second leukocyte under conditions to allow a pro-inflammatory allorecognition to provide a conditioned preparation, wherein the first leukocyte is allogeneic to the second leukocyte; (ii) removing the first leukocyte and the second leukocyte from the conditioned preparation under conditions to inhibit RNA degradation so as to obtain a composition enriched in acellular pro-inflammatory components; and (iii) formulating the composition of step (ii), under conditions to inhibit RNA degradation, in the pro-inflammatory preparation for administration to the subject. The administration of the pro-inflammatory preparation is intended to decrease the Treg/Tinflam ratio in the subject. In an embodiment, the process further comprises, prior to step (i), associating a low-immunogenic biocompatible polymer to a cytoplasmic membrane of at least one of the first leukocyte or the second leukocyte. In another embodiment, the process further comprises covalently binding the low-immunogenic biocompatible polymer to a membrane-associated protein of the cytoplasmic membrane of the at least one of the first leukocyte or the second leukocyte. In still another embodiment, the low-immunogenic biocompatible polymer is a polyethylene glycol (PEG), for example a methoxy polyethylene glycol (mPEG). In still another embodiment, the process further comprises covalently binding the mPEG by contacting the first leukocyte and/or the second leukocyte with methoxy-poly(-ethylene glycol) succinimidyl valerate. In an embodiment, step (ii) of the process occurs in vitro, for example by culturing the first leukocyte and the second leucocyte. In this embodiment, the pro-inflammatory preparation will be derived from the supernatant of the cell culture. In yet another embodiment, the process further comprises, prior to step (ii), preventing one of the first leukocyte or the second leukocyte from proliferating. In another embodiment, step (ii) of the process occurs in vivo, for example by administering the first leukocyte to a mammal having the second leukocyte. In this embodiment, the pro-inflammatory preparation will be derived from the plasma of the mammal. In still another embodiment, the process further comprises preventing the first leukocyte from proliferating prior to administration to the mammal. In yet another embodiment, step (ii) of the process further comprises removing components having an average molecular weight of more than about 10 kDa from the conditioned preparation, for example by filtering out components having the average molecular weight of more than about 10 kDa from the conditioned preparation. In still another example, step (ii) of the process further comprises enriching the conditioned preparation in at least one miRNA species. In another embodiment, step (iv) of the process further comprises formulating the composition for intravenous administration to the subject. In some embodiments, the first leukocyte and/or the second leukocyte is a T cell (such as a CD4-positive T cell or a CD8-positive T cell). In an embodiment, the decreased ratio between the level of Treg cells and the level of pro-inflammatory T cells is for treating, preventing and/or alleviating the symptoms associated with a condition caused by or exacerbated by a reduced immune response in the subject. In an embodiment, the condition is a proliferation-associated disorder and/or an infection. In an embodiment, the proliferation-associated disorder is cancer. In still a further embodiment, the decreased ratio between the level of Treg cells and the level of pro-inflammatory T cells is for limiting the growth of a malignant tumor and/or for reducing the size of a malignant tumor. In yet another embodiment, the infection is a parasitic infection, a viral infection, a bacterial infection and/or a fungal infection.

According to a fourth aspect, there is provided a pro-inflammatory preparation for decreasing a ratio of the level of regulatory T (Treg) cells to the level of pro-inflammatory T cells in a subject, wherein the pro-inflammatory preparation is obtained by the process described herein. In an embodiment, the pro-inflammatory preparation has at least one, five, ten or more miRNA species presented in FIG. 9. In still another embodiment, the pro-inflammatory preparation has at least one, five, ten or more of the miRNA species listed any one of Tables 1A to 1 D. In yet another embodiment, the pro-inflammatory preparation has at least one, five, ten or more of the miRNA species listed in any one of Tables 2A to 2D. In yet another embodiment, the pro-inflammatory preparation has at least one, five, ten or more of the miRNA species identified in any one of FIGS. 8A to 8C. In a further embodiment, the decreased ratio between the level of Treg cells and the level of pro-inflammatory T cells is for treating, preventing and/or alleviating the symptoms associated with a condition caused or exacerbated by a reduced immune response in the subject. In an embodiment, the condition is a proliferation-associated disorder and/or an infection. In an embodiment, the proliferation-associated disorder is cancer. In still a further embodiment, the decreased ratio between the level of Treg cells and the level of pro-inflammatory T cells is for limiting the growth of a malignant tumor and/or for reducing the size of a malignant tumor. In yet another embodiment, the infection is a viral infection, a bacterial infection and/or a fungal infection.

Throughout this text, various terms are used according to their plain definition in the art. However, for purposes of clarity, some specific terms are defined below.

Allogeneic cell. A cell is considered "allogeneic" with respect to another cell if both cells are derived from the same animal species but presents sequence variation in at least one genetic locus. A cell is considered "allogeneic" with respect to a subject if the cell is derived from the same animal species as the subject but presents sequence variation in at least one genetic locus when compared to the subject's respective genetic locus. Allogeneic cells induce an immune reaction (such as a cell-based immune reaction, a rejection for example) when they are introduced into an immunocompetent host. In an embodiment, a first cell is considered allogeneic with respect to a second cell if the first cell is HLA-disparate (or HLA-mismatched) with the second cell.

Allo-recognition. As it is known in the art, the term "allo-recognition" (also spelled allorecognition) refers to an immune response to foreign antigens (also referred to as alloantigens) from members of the same species and is caused by the difference between products of highly polymorphic genes. Among the most highly polymorphic genes are those encoding the MHC complex which are most highly expressed on leukocytes though other polymorphic proteins may similarly result in immune recognition. These polymorphic products are typically recognized by T cells and other mononuclear leukocytes. In the context of the present invention, the term "pro-inflammatory allo-recognition" refers to an immune response associated with the expansion of pro-inflammatory T cells and/or the differentiation of naïve T cells into pro-inflammatory T cells. Pro-inflammatory allo-recognition in vivo mediates cell or tissue injury and/or death and loss of cell or tissue function. Still in the context of the present invention, the term "pro-tolerogenic allo-recognition" refers to an immune response associated with the expansion of Treg cells and/or the differentiation of naïve T cells into Treg cells and/or a decrease in the expansion of pro-inflammatory T cells (e.g., Th1, Th17 cells) and/or differentiation of naïve T cells to pro-inflammatory T cells. A pro-tolerogenic allo-recognition is usually considered weaker than a pro-inflammatory allo-recognition. Further, an in vivo pro-tolerogenic allo-recognition does not lead to significant cell or tissue injury and/or death nor loss of cell or tissue function.

Anergy and Tolerance. In the present context, the term "anergy" refers to a non-specific state of immune unresponsiveness to an antigen to which the host was previously sensitized to or unsensitized to. It can be characterized by a decrease or even an absence of lymphokine secretion by viable T cells when the T cell receptor is engaged by an antigen. In the present context, the term "tolerance" (also referred to as a pro-tolerogenic state) refers to an acquired specific failure of the immunological mechanism to respond to a given antigen, induced by exposure to the antigen (e.g., a tumor antigen for example). Tolerance refers to a specific nonreactivity of the immune system to a particular antigen, which is capable, under other conditions, of inducing an immune response. However, in the present context, the terms "anergy" and "tolerance" are used interchangeably since the compositions and methods presented herewith can be used to achieve both anergy and tolerance.

Autologous cell. A cell is considered "autologous" with respect to another cell if both cells are derived from the same individual or from genetically identical twins. A cell is considered "autologous" to a subject, if the cell is derived from the subject or a genetically identical twin. Autologous cells do not induce an immune reaction (such as a rejection) when they are introduced into an immuno-competent host.

Conditions associated with a reduced (low or inappropriate) immune response. In the context of the present invention, the subjects afflicted by these conditions have increased ratio of Treg to pro-inflammatory T cells when compare to the same ratio of sex- and age-matched healthy subjects. Alternatively, the subjects afflicted by these conditions may have normal ratios of Treg to pro-inflammatory T cells but exhibit a reduced to absent proinflammatory response to antigenic stimuli. In some embodiments, the immune system of subjects afflicted by a condition associated with a low, repressed or inappropriate immune response is in a state of anergy. The immune system of some of the subjects afflicted by these conditions fails to produce target specific pro-inflammatory cell (T and B lymphocytes) capable of recognizing and destroying abnormal cells (e.g., cancer cells or infected cells). Alternatively, the immune system of some of the subjects afflicted by these conditions exhibit elevated levels of regulatory T and B cells that inhibit normal pro-inflammatory T and B cells from exerting their function (i.e. inducing a partial or complete immune suppression) thereby preventing destruction of an abnormal cell of cell aggregates. One of these conditions is a proliferation-associated disorder (such as, for example, cancer). Another of these conditions is an infection (such as for example a parasitic infection).

Immune stimulation. In the present context, the term "immune stimulation" or "pro-inflammatory state" refers to a state of immune responsiveness to an antigen independent of the host previous sensitization to the antigen. It can be characterized by an increase or a modulation in the level of lymphokine secretion by viable T cells when the T cell receptor is engaged by an antigen. In the present context, the term "stimulation" refers to an acquired specific activation of the immunological mechanism to respond to a given antigen, induced by exposure to the antigen. In the context of the present invention, the immune stimulation is considered therapeutic and specifically excludes inflammatory diseases, conditions and/or disorders.

Immunogenic cell. A first cell is considered immunogenic with respect to a second cell when it is able to induce an immune response in the latter cell. In some embodiment, the immune response is in vitro (e.g., a mixed lymphocyte reaction) or can be observed in vivo (e.g., in a subject having the second cell and having received the first cell). The second cell can be located in an immunocompetent subject. Preferably, the immune response is a cell-based immune response in which cellular mediator can be produced. In the context of this invention, the immunogenic cells are immune cells, such as white blood cells or leukocytes.

Immunogenic cell culture conditions. A cell culture is considered to be conducted in immunogenic conditions when it allows the establishment of a pro-inflammatory immune response between two distinct and unmodified leukocytes (and, in an embodiment, allo-recognition). Preferably, the pro-inflammatory immune response is a cell-based immune response in which cellular mediator can be produced. For example, the cell culture conditions can be those of a mixed lymphocyte reaction (primary or secondary).

Infection. As used in the context of the present invention, the term "infection" or "infective disease" is a condition caused by the presence and proliferation of an infectious agent which induces a state of low or repressed immune response (e.g., anergy). In some embodiments, the infection is caused by a parasite and in such instances, it is referred to as a "parasitic" infection. There are mainly three classes of parasites which can cause infections, at least in humans, protozoa (causing protozoan infection), helminths (causing an helminthiasis) and ectoparasites. As it is known in the art, parasites have the intrinsic ability, upon infecting their host, to upregulate or enhance Treg's levels and/or activity and thereby induce a state of immune tolerance. This is exemplified by filarial nematodes in which the nematode secretes substances that cause an increase in the host's Treg lymphocytes levels. The increase in Tregs actively down-regulate the Th1, Th17 and Th2 responses necessary for eradication of the parasite. Administration of an agent that can reverse the parasite's induced Treg increase would enhance the ability of the subjects immune system to eradicate the parasitic infection. In another embodiment, the infection is caused by a virus (such as, for example, the human immunodeficiency virus or HIV) and, in such instance, it is referred to as a "viral" infection. In some embodiments, the viral infection is an acquired immunodeficiency syndrome or AIDS. In yet another embodiment, the infection is caused by a bacteria (such as, for example, from a *Streptococcus* sp. (e.g., *Streptococcus pneumoniae*) and, in such instance, it is referred to as a "bacterial" infection. In some embodiments, the bacterial infection is a pneumonia. As it is known in the art, Tregs are implicated in both improving clearance and reducing injury due to bacteria/viruses as well as increasing infections in viruses and bacteria. Viral and bacterial infections spread can be facilitated by an overly strong immune response, hence Tregs would reduce this risk. However, elevated Treg, in the absence of a proinflammatory response, would cause a state of immune suppression. In another embodiment, the infection is caused by a fungus and, in such instances, it is referred to as a "fungal" infection. Fungal infections are opportunistic and T cells play a critical role in stimulating the neutrophils which are able to limit or clear the fungal infection. Subjects with a reduced (low or inappropriate) immune response have an increased risk towards fungal infections (e.g., *Aspergillus* sp. (e.g. *Aspergillus histoplasmosis*) and *Candidia* sp. (e.g., *Candida albicans*)).

Leukocyte. As used herein, a leukocyte (also spelled leucocyte) is defined as a blood cell lacking hemoglobin and having a nucleus. Leukocytes are produced and derived from hematopoietic stem cells. Leukocytes are also referred to as white blood cells. Leukocytes include granulocytes (also known as polymorphonuclear leucocytes), e.g., neutrophils, basophils and eosoniphils. Leukocytes also include agranulocytes (or mononuclear leucocytes), e.g., lymphocytes, monocytes and macrophages. Some of the lymphocytes, referred to as T cells (or T-cell), bear on their surface a T-cell receptor. T cell are broadly divided into cells expressing CD4 on their surface (also referred to as CD4-positive cells) and cells expressing CD8 on their surface (also referred to as CD8-positive cells). Some of the lymphocytes, referred to as B cells (or B-cells), bear on their surface a B-cell receptor.

Low-immunogenic biocompatible polymer. As used herein, a "low-immunogenic polymer" refers to a polymer which is not or is unlikely to elicit an immune response in an individual. This low-immunogenic polymer is also capable, when grafted at the appropriate density, of masking an antigenic determinant of a cell and lowering or even preventing an immune response to the antigenic determinant when the antigenic determinant is introduced into a subject. A "biocompatible polymer" refers to a polymer which is non-toxic when introduced into a subject. Exemplary low-immunogenic biocompatible polymers includes, but are not limited to, polyethylene glycol (for example methoxypoly (ethylene glycol)), hyperbranched polyglycerol (HPG) and 2-alkyloxazoline (POZ).

Non-proliferative leukocyte. As used herein, the term "non-proliferative leukocyte" refers to a leukocyte which has been modified to no longer being capable of cellular proliferation (e.g. performing at least one complete division cycle). In some embodiments, this modification may be temporary and the non-proliferative properties of a leukocyte may be limited in time. For example, when a leukocyte is modified from a contact with a pharmacological agent capable of limiting its proliferation, the removal of the pharmacological agent from the cell culture can allow the leukocyte to regain its proliferative properties. In other embodiments, the modification is permanent and the modified leukocyte cannot regain its proliferative properties. For example, when a leukocyte is irradiated, it is not possible for it to regain its proliferative properties. In the context of the present application, the expressions "non-proliferative leukocyte" or "leukocyte limited from proliferating" are used interchangeably.

Peripheral blood mononuclear cells (PBMC). This term refers to the cell population recuperated/derived from the peripheral blood of a subject (usually a mammal such as a human). PBMC usually contains T cells, B cells and antigen presenting cells.

Pharmaceutically effective amount or therapeutically effective amount. These expressions refer to an amount (dose) of an acellular preparation effective in mediating a therapeutic benefit to a patient (for example prevention, treatment and/or alleviation of symptoms of an immune-associated disorder or infection in which the ratio of Tregs to pro-inflammatory T cells is high when compared to sex- and aged-matched healthy subjects or in which a reduced/absent proinflammatory response to antigenic stimuli is observed). It is also to be understood herein that a "pharmaceutically effective amount" may be interpreted as an amount giving a desired therapeutic effect, either taken in one dose or in any dosage or route, taken alone or in combination with other therapeutic agents.

Prevention, treatment and alleviation of symptoms. These expressions refer to the ability of the acellular preparation to limit the development, progression and/or symptomology of a immune-associated disorder associated to conditions caused/exacerbated by a low or inappropriate immune response (also known as a state of anergy or tolerance). The subjects being afflicted with these conditions/disorders have a ratio of Tregs to pro-inflammatory T cells which is considered high when compared to sex- and aged-matched healthy subjects. Broadly, the prevention, treatment and/or alleviation of symptoms encompasses decreasing the levels of Treg cells and/or increasing the levels of pro-inflammatory T cells. The acellular-based preparation is considered effective or successful for treating and/or alleviating the symptoms associated with the disorder when a reduction in the pro-tolerogenic state (when compared to an untreated and afflicted individual) in the treated individual (previously known to be afflicted with the disorder) is observed. A method or acellular-based preparation is considered effective or successful for preventing the disorder when a reduction in the pro-tolerogenic state (when compared to an untreated and afflicted individual) in the treated individual is observed upon an immunological challenge (such as, for example, an antigenic challenge). In instances where the conditions to be treated is cancer, exemplary symptoms which can be alleviated with the acellular-based preparations described herewith include, but are not limited to, number and/or size of metastasic tumors, presence and/or spread of metastatic tumors and/or size of primary tumor. In instances where the conditions to be treated is an infection, exemplary symptoms which can be alleviated with the acellular-based preparations described herewith include, but are not limited to, infectious agent's burden, infectious agent's presence and fever.

Pro-inflammatory T cells. In the present context, pro-inflammatory T cells are a population of T cells capable of mediating an inflammatory reaction. Pro-inflammatory T cells generally include T helper 1 (Th1 or Type 1) and T helper 17 (Th17) subsets of T cells. Th1 cells partner mainly with macrophage and can produce interferon-γ, tumor necrosis factor-β, IL-2 and IL-10. Th1 cells promote the cellular immune response by maximizing the killing efficacy of the macrophages and the proliferation of cytotoxic CD8+ T cells. Th1 cells can also promote the production of opsonizing antibodies. T helper 17 cells (Th17) are a subset of T helper cells capable of producing interleukin 17 (IL-17) and are thought to play a key role in autoimmune diseases and in microbial infections. Th17 cells primarily produce two main members of the IL-17 family, IL-17A and IL-17F, which are involved in the recruitment, activation and migration of neutrophils. Th17 cells also secrete IL-21 and IL-22.

Proliferation-associated disorders. These disorders (also referred to as hyperproliferative disorders) form a class of diseases where cells proliferate more rapidly, and usually not in an ordered fashion, than corresponding healthy cells. The proliferation of cells cause an hyperproliferative state that may lead to biological dysfunctions, such as the formation of tumors (malignant or benign). One of the proliferation-associated disorder is cancer. Also known medically as a malignant neoplasm, cancer is a term for a large group of different diseases, all involving unregulated cell growth. In cancer, cells divide and grow uncontrollably, forming malignant tumors, and invade nearby parts of the body. The cancer may also spread to more distant parts of the body through the lymphatic system or bloodstream. In an embodiment, the cancer is a carcinoma (e.g. a cancer of the epithelial cells). Other types of cancer include, but are not limited to sarcoma, lymphoma, leukemia, germ cell tumor and blastoma.

Regulatory T cells. Regulatory T cells are also referred to as Treg and were formerly known as suppressor T cell. Regulatory T cells are a component of the immune system that suppress immune responses of other cells. Regulatory T cells usually express CD3, CD4, CD8, CD25, and Foxp3. Additional regulatory T cell populations include Tr1, Th3, CD8$^+$CD28$^-$, CD69$^+$, and Qa-1 restricted T cells. It has been recently shown that CD69 can exert regulatory function in the immune response by preventing pro-inflammatory conditions. Under normal conditions, this regulatory effect of CD69 is desired, but when expressed in the context of a pro-inflammatory response to, for example, a tumor cell mass, will result in impaired killing of the abnormal cells and disease progression. Regulatory T cells actively suppress activation of the immune system and prevent pathological self-reactivity, i.e. autoimmune disease. The critical role regulatory T cells play within the immune system is evidenced by the severe autoimmune syndrome that results from a genetic deficiency in regulatory T cells. The immunosuppressive cytokines TGF-β and Interleukin 10 (IL-10) have also been implicated in regulatory T cell function. Similar to other T cells, a subset of regulatory T cells can develop in the thymus and this subset is usually referred to as natural Treg (or nTreg). Another type of regulatory T cell (induced Treg or iTreg) can develop in the periphery from naïve CD4$^+$ T cells. The large majority of Foxp3-expressing regulatory T cells are found within the major histocompatibility complex (MHC) class II restricted CD4-expressing (CD4$^+$) helper T cell population and express high levels of the interleukin-2 receptor alpha chain (CD25). In addition to the Foxp3-expressing CD4$^+$CD25$^+$, there also appears to be a minor population of MHC class I restricted CD8$^+$ Foxp3-expressing regulatory T cells. Unlike conventional T cells, regulatory T cells do not produce IL-2 and are therefore anergic at baseline. Moreover, regulatory T cell produce elevated levels of IL-10 and TGF-β which inhibit pro-inflammatory responses An alternative way of identifying regulatory T cells is to determine the DNA methylation pattern of a portion of the foxp3 gene (TSDR, Treg-specific-demthylated region) which is found demethylated in Tregs.

Splenocytes. This term refers to the cell population obtained from the spleen of a subject (usually a mammal such as a rodent). Splenocytes usually comprise T cell, B cell as well as antigen presenting cells.

Syngeneic cell. A cell is considered "syngeneic" with respect to a subject (or a cell derived therefrom) if it is sufficiently identical to the subject so as to prevent an immune rejection upon transplantation. Syngeneic cells are derived from the same animal species.

Viable. In the present context, the term "viable" refers to the ability of a cell to complete at least one cell cycle and, ultimately proliferate. A viable cell is thus capable of proliferating. By opposition, the term "non-viable" or "non-proliferative" both refer to a cell which is no longer capable of completing at least one cell cycle. By comparison, the term "cycle arrest" refers to a cell which has been treated to halt its cell cycle progression (usually with a pharmacological agent) but which is still capable of re-entering the cell cycle (usually when the pharmacological agent is removed).

Xenogeneic cell. A cell is considered "xenogeneic" with respect to a subject (or a cell derived from the subject) when it is derived from a different animal species than the subject. A xenogeneic cell is expected to be rejected when transplanted in an immunocompetent host.

BRIEF DESCRIPTION OF THE DRAWINGS

Having thus generally described the nature of the invention, reference will now be made to the accompanying drawings, showing by way of illustration, a preferred embodiment thereof.

FIG. 5 illustrates the effects of the IA preparations on the phosphorylation of phosphokinases of resting Jurkat cells. Results are shown as fold modulation (when compared to saline-treated Jurkat cells) for each kinase tested.

1 has-miR-298
2 has-miR-34a-5p
3 has-miR-574-3p
4 has-miR-125b-5p
5 has-let-7a-5p
6 has-miR-196a-5p
7 has-miR-148a-3p
8 has-let-7e-5p
9 has-miR-134

Figure 9:
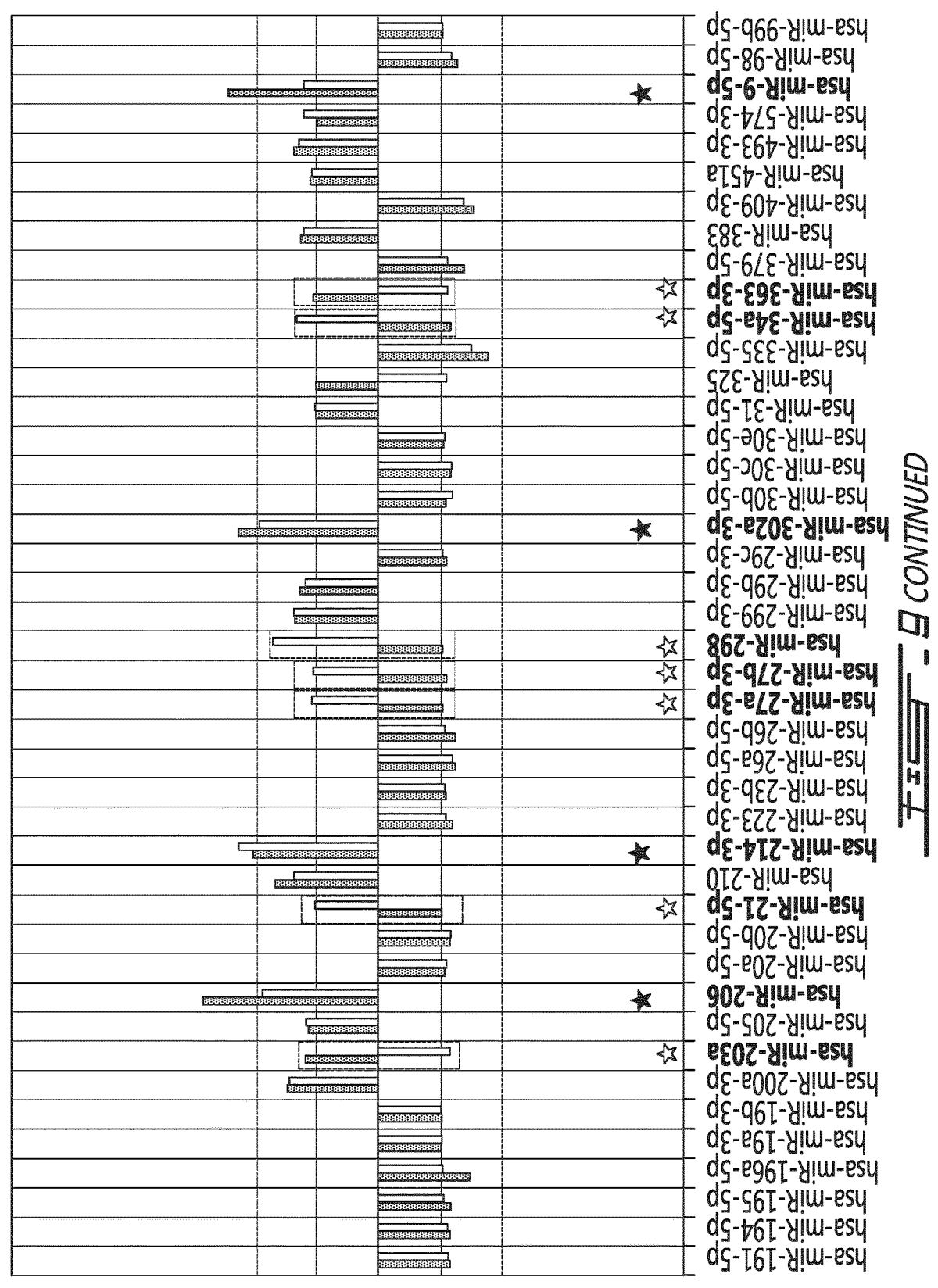

FIG. 9 provides a partial miRNA compositional analysis of the conditioned medium of a mPEG MLR (white bars) and of a control MLR (black bars). Results are provided, for each miRNA, as $\log_2$ fold regulation when compared to the miRNA present in the supernatant of resting cells. White open stars denote $\log_2$-fold change and black solid stars denote significant changes in volcano plot analysis.

Figure 10:
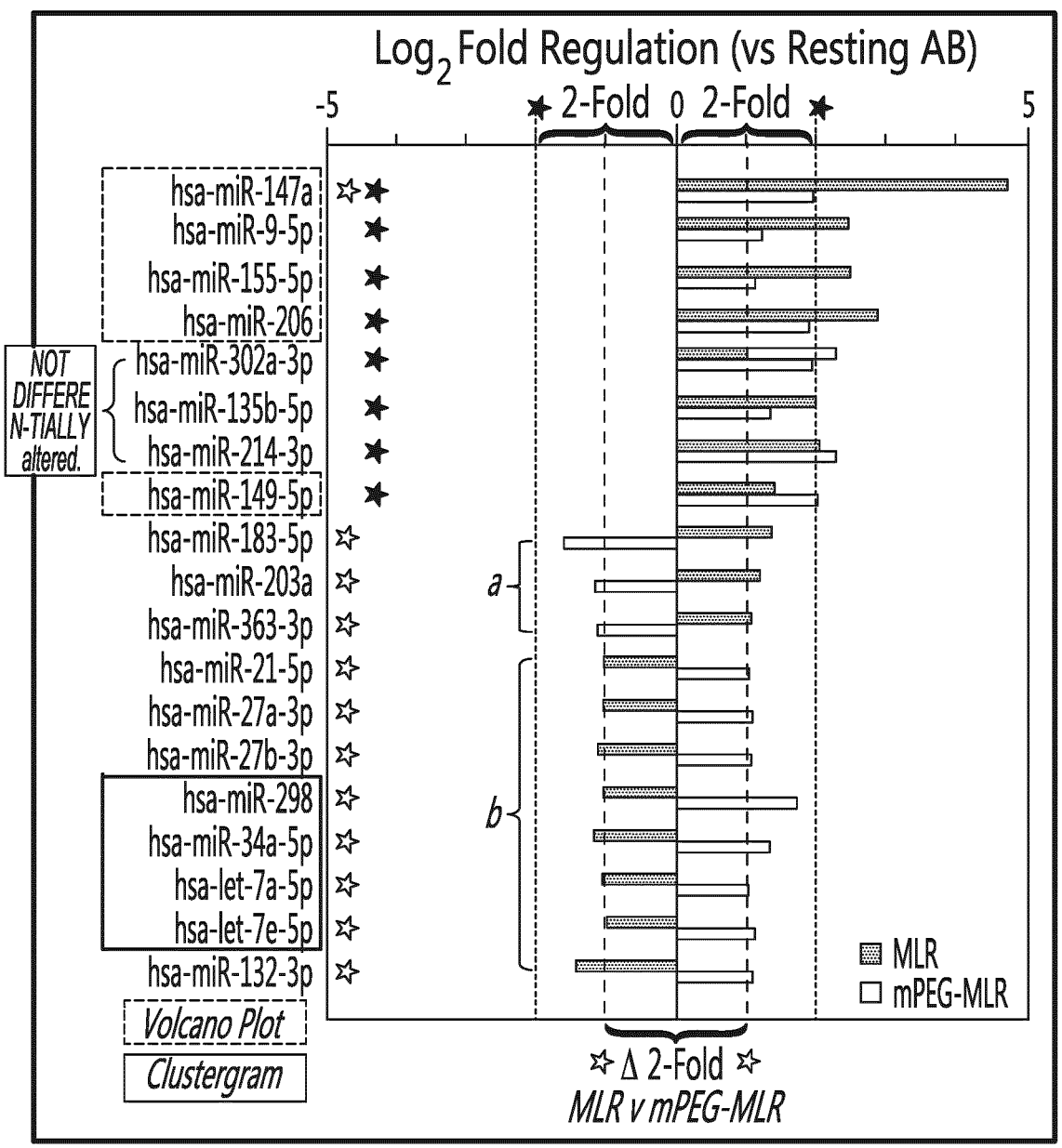

FIG. 10 provides a selection of the miRNA compositional analysis of the conditioned medium of a mPEG MLR (white bars) and of a control MLR (black bars). Results are provided, for each miRNA, as $\log_2$ fold regulation when compared to the miRNA present in the supernatant of resting cells. White open stars denote $\log_2$-fold change and black solid stars denote significant changes and or clustergram (heatmap) determined miRNA shifts denoted in volcano plot analysis.

DETAILED DESCRIPTION

In accordance with the present invention, there are provided acellular preparations for decreasing the level of regulatory T cells and/or increasing the level of pro-inflammatory T cells for inducing immune stimulation and/or a pro-inflammatory state in a subject in need thereof. The acellular-based preparations and therapies presented are achieved by contacting at least two distinct leukocyte populations which are considered allogeneic with respect to one another. The contact between the two leukocyte populations occurs under conditions to allow pro-inflammatory allo-recognition but limit or prevent pro-tolerogenic recognition. The acellular components produced by contacting the two leukocyte populations can optionally be purified or enriched to provide a preparation enriched in miRNAs. In embodiments, the acellular preparation can also be processed to (substantially) remove cells, cells fragments as well as secreted proteins (such as cytokines for example). The contact between the two leukocyte populations can occur in vitro, ex vivo or in vivo.

These acellular preparations induce a state of (complete or partial) immune stimulation. As such these acellular preparations can be useful for decreasing the levels of regulatory T cells and/or increasing the levels of pro-inflammatory T cells in subjects in need thereof.

Since the acellular preparations can optionally be enriched in miRNAs, it is important that the cell culture and/or the blood/blood fraction be processed in conditions so as to retain the integrity of the majority of the miRNA species present, for example by substantially inhibiting RNA degradation. As used herein, the term "substantially inhibiting RNA degradation" indicate that the conditions allow for the degradation of less than 20%, 19%, 18%, 17%, 16%, 15%, 14%, 13%, 12%, 11%, 10%, 9%, 8%, 7%, 6% or 5% of the miRNA population obtained by RNases. RNases include, but are not limited endoribonucleases (e.g., RNase A, RNase H, RNase I, RNase III, RNase L, RNase P, RNase PhyM, RNase T1, RNase T2, RNase U2, RNase V1 and/or RNase V) and exoribonucleases (e.g., polynucleotide pPhosphorylase (PNPase), RNase PH, RNase II, RNase R, RNase D, RNase T, Oligoribonuclease, Exoribonuclease I and/or Exoribonuclease II). Since it is known in the art that miRNAs are, in general, more resistance towards degradation than messenger RNAs, the conditions for obtaining and processing the cell culture/blood can allow for some RNA degradation, preferably limited to the mRNA fraction.

As it will be shown below, acellular preparations obtained from allogeneic leukocytic cells provides a significant opportunity to modulate the responsiveness (i.e., immunoquiescent versus pro-inflammatory) of the recipient's immune system. Without wishing to be bound to theory, it is hypothesized that the acellular preparations obtained can be used to attenuate Tregs differentiation/expansion and/or increase Th17/Th1 and pro-inflammatory cytokine secretion to prevent or lower a pro-tolerogenic immune response.

More specifically, and as shown herein, the acellular preparations derived from allogeneic leukocytes cause an enhanced pro-inflammatory (i.e., anti-tumor) response can. The acellular preparations can increase Th1/Th17 response (e.g., numbers and/or responsiveness). Further, the acellular preparations can augment/replicate this inflammatory response by increasing NK (natural killer) cell counts. NK cells play critical roles in host immunity against cancer and it is known that, in various cancers, the subjects can develop immunomodulatory mechanisms to escape NK cell attack and/or induce defective NK cell responses. In addition, the acellular preparations can decrease various classes Treg cell levels, including Foxp3$^+$, CD25$^+$ and CD69$^+$ cell counts. The results indicate that the acellular preparations can be useful in inducing a pro-inflammatory state in cancer subjects as well as in response against infectious agents and mediate useful therapeutic effects.

Processes for Obtaining Acellular Preparations

The acellular preparations presented described herein can be obtained by contacting two distinct and allogeneic leukocyte populations (referred herein to the first leukocyte and the second leukocyte). The two leukocyte populations are contacted under conditions so as to allow (and in some embodiments to favor) pro-inflammatory allo-recognition and to prevent (and in some embodiments to inhibit) pro-tolerogenic allo-recognition.

In some embodiments, it is possible that the first and/or the second leukocyte be modified to bear on their surface a low-immunogenic polymer. In such embodiment, it is important that the polymer grafted or the conditions used to graft the polymer do not significantly alter the ability of the two leukocyte populations to mediate a pro-inflammatory allo-recognition. It is important that the polymer used exhibits both low-immunogenicity and biocompatibility once introduced into a cell culture system or administered to the test subject. Polyethylene glycol (particularly methoxypoly (ethylene glycol)), 2-alkyloxazoline (POZ) and hyperbranched polyglycerol (HPG) are exemplary polymers which all exhibit low immunogenicity and biocompatibility and can be successfully used to modify the first leukocyte (and optionally the second leukocyte). In some embodiments, it is preferable to use a single type of polymer to modify the surface of leukocytes. In other embodiments, it is possible to use at least two distinct types of polymers to modify the surface of the leukocyte.

In an embodiment, the low-immunogenic biocompatible polymer can be covalently associated with the membrane-associated protein(s) of the leukocyte by creating a reactive site on the polymer (for example by deprotecting a chemical group) and contacting the polymer with the leukocyte. For example, for covalently binding a methoxypoly(ethylene glycol) to the surface of a leukocyte, it is possible to incubate a methoxypoly(-ethylene glycol) succinimidyl valerate (reactive polymer) in the presence of the leukocyte. The contact between the reactive polymer and the leukocyte is performed under conditions sufficient for providing a grafting density which will allow pro-inflammatory allo-recognition and prevent pro-tolerogenic allo-recognition. In an embodiment, the polymer is grafted to a viable leukocyte and under conditions which will retain the viability of the leukocyte. A linker, positioned between the surface of the leukocyte and the polymer, can optionally be used. Examples of such polymers and linkers are described in U.S. Pat. Nos. 5,908,624; 8,007,784 and 8,067,151. In another embodiment, the low-immunogenic biocompatible polymer can be integrated within the lipid bilayer of the cytoplasmic membrane of the leukocyte by using a lipid-modified polymer.

As indicated above, it is important that the low-immunogenic biocompatible polymer be grafted at a density sufficient allowing pro-inflammatory allo-recognition while preventing pro-tolerogenic allo-recognition of the first leukocyte by the second leukocyte (and vice versa). In an embodiment, the polymer is polyethylene glycol (e.g., linear) and has an average molecular weight between 2 and 40 KDa as well as any combinations thereof. In an embodiment, the polymer is polyethylene glycol (e.g. linear) and has an average molecular weight between 2 and 40 KDa as well as any combinations thereof. In a further embodiment, the average molecular weight of the PEG to be grafted is at least 2, 3, 4, 5, 10, 15, 20, 25, 30, 35 or 40 kDa. In another embodiment, the average molecular weight of the PEG to be granted is no more than 40, 35, 30, 25, 20, 15, 10, 5, 4, 3, or 2 kDa. In another embodiment, the grafting concentration of the polymer (per $20 \times 10^6$ cells) is no more than 2.4, 2.0, 1.0, 0.5, 0.4, 0.3, 0.2, 0.1, 0.05, 0.01 or 0.005 mM. In still another embodiment, the grafting concentration of the polymer (per $20 \times 10^6$ cells) is equal to or lower than 0.005, 0.01, 0.05, 0.1, 0.2, 0.3, 0.4, 0.5, 1.0, 2.0, 2.4 mM. In embodiments where the polymer is grafter to affect the viability of the leukocyte (for example by creating cellular instability, cellular fragmentation or vesiculization, the concentration of the polymer (per $20 \times 10^6$ cells) is equal to or higher than 10 mM. In order to determine if pro-inflammatory allo-recognition occurs, various techniques are known to those skilled in the art and include, but are not limited to, a standard mixed lymphocyte reaction (MLR), high molecular weight mitogen stimulation (e.g. PHA stimulation) as well as flow cytometry (Chen and Scott, 2006). In order to determine if a pro-tolerogenic allo-recognition occurs, various techniques are known to those skilled in the art and include, but are not limited to, the assessment of the level of expansion and differentiation of Treg cells and or prevention of Th17 expansion/differentiation.

Before or after being modified with a low-immunogenic and biocompatible polymer, the first leukocyte can be optionally modified to refrain from being proliferative. This modification preferably occurs prior to its introduction in a cell culture system or its administration into a test subject. For example, the leukocyte can be irradiated (e.g. γ-irradiation) prior to its introduction in a cell culture system or in the test subject. Upon irradiation, the leukocyte is not considered viable (e.g. capable of proliferation). In an embodiment, polymer grafting can affect the leukocyte viability and be used to refrain the leukocyte from proliferating. Alternatively, leukocyte can be treated with a pharmacological agent which halts cell cycle progression. Upon the administration of such pharmacological agent, the leukocyte is considered viable since it can resume cellular proliferation when the agent is removed from the cell-containing medium.

It is also contemplated that the second leukocyte (which can optionally be modified with the low-immunogenic and biocompatible polymer) be also optionally modified to refrain from being proliferative. For example, the leukocyte can be irradiated (e.g. γ-irradiation) prior to its introduction in a cell culture system or in the test subject. Upon irradiation, the leukocyte is not considered viable (e.g. capable of proliferation). In an embodiment, polymer grafting can affect the leukocyte viability and can be used to refrain the leukocyte from proliferating. Alternatively, leukocyte can be treated with a pharmacological agent which halts cell cycle progression. Upon the administration of such pharmacological agent, the leukocyte is considered viable since it can resume cellular proliferation when the agent is removed from the cell-containing medium. However, when the second leukocyte is modified from being proliferative, it is important the first leukocyte with which it is being contacted remains proliferative.

In order to generate the acellular preparation, it is not necessary to provide homogeneous leukocyte populations. For example, the first leukocyte population (such as, for example a PBMCs or splenocytes) can be introduced in a cell culture system and contacted with a second leukocyte population (such as, for example a PBMCs or splenocytes) or administered to the test subject. However, in some embodiments, it is possible to provide and contact a more homogeneous leukocyte populations. For example, the first leukocyte population can be relatively homogenous (such as, for example, a T cell population) and introduced in a cell culture system comprising a second leukocyte (such as, for example a PBMC or splenocyte) or administered to the test subject. In another example, the first leukocyte population (such as, for example a PBMC or splenocyte) can be introduced in a cell culture system comprising a second leukocyte population which can be relatively homogeneous (such as, for example, a T cell population). In a further example, the first leukocyte population can be relatively homogenous (such as, for example, a T cell population) and introduced in a cell culture system comprising a second leukocyte population which can be relatively homogeneous (such as, for example, a T cell population).

To provide the acellular preparations described herewith, the leukocytes used can be mature leukocytes or be provided in the form of stem cells (e.g, for example non-embryonic stem cells). For example, leukocytes can be obtained from isolating peripheral blood mononuclear cells (PBMC) from the subject. Optionally, the PBMCs can be differentiated in vitro into dendritic (DC) or DC-like cells. Alternatively, the leukocytes can be obtained from the spleen (e.g. splenocytes). Leukocytes usually include T cells, B cells and antigen presenting cells. In some embodiments, cells of sufficient antigenic variation and immunogenicity are used. In addition, for providing the acellular preparations, the leukocytes but not erythrocytes are necessary since the polymer-modified erythrocytes are not capable of eliciting a pro-inflammatory allo-recognition when administered in a test subject. However, traces of erythrocytes in the leukocyte population used are tolerated (for example, less than about 10%, less than about 5% or less than about 1% of the total number of cells in the preparation).

Even though it is not necessary to further purify the leukocytes to provide the acellular preparations, it is possible to use a pure cell population or a relatively homogenous population of cells as leukocytes. This "pure" cell population and "relative homogenous population" of cells can, for example, essentially consist essentially of a single cell type of T cells, B cells, antigen presenting cells (APC) or stem cells. Alternatively, the population of cells can consist essentially of more than one cell type. The population of cells can be obtained through conventional methods (for example cell sorting or magnetic beads). In an embodiment, when the population of cells consist of a single cell type (for example, T cells), the percentage of the cell type with respect to the total population of cells is at least 90%, at least 95% or at least 99%. The relatively homogenous population of cells are expected to contain some contaminating cells, for example less than 10%, less than 5% or less than 1% of the total population of cells.

The first leukocyte and/or second leukocyte can be obtained from any animals, but are preferably derived from mammals (such as, for example, humans and mice). In an embodiment, the first and/or second leukocyte can be obtained from a subject intended to be treated with the acellular preparation.

The first and/or second leukocyte can be expanded in vitro prior to the introduction in a cell culture system or the administration to a test subject.

As indicated above, the first and the second leukocyte are contacted under conditions to allow pro-inflammatory allo-recognition (e.g. expansion of pro-inflammatory T cells and/or differentiation of naïve T cells in pro-inflammatory T cells) and prevent/inhibit pro-tolerogenic allo-recognition (e.g. expansion of Treg cells and/or differentiation of naïve T cells in Treg cells). When the contact occurs in vitro, it is important that the first leukocyte and the second leukocyte be cultured under conditions allowing physical contact between the two leukocyte populations and for a time sufficient to provide a conditioned medium. As used herein, a conditioned medium refers to physical components of a cell culture (or fraction thereof, such as the cell culture supernatant) obtained by contacting the first and the second leukocyte and having the pro-tolerogenic properties described herein. Usually, the conditioned medium is obtained at least 24 hours after the initial contact between the first and the second leukocyte. In some embodiment, the conditioned medium is obtained at least 48 hours or at least 72 hours after the initial contact between the first and the second leukocyte. In an embodiment, the conditioned medium can be obtained after at least 24 hours of incubating a first leukocyte with a second leukocyte. When the incubation takes place in a 24-well plate, the concentration of each leukocyte population can be, for example, at least $1 \times 10^6$ cells.

When the contact occurs in vivo, it is important that the first leukocyte be administered to an immune competent test subject (bearing the second leukocyte) and that the blood or blood fraction be obtained at a later a time sufficient to provide a conditioned blood. The test subject is a subject being immune competent and having a Treg/pro-inflammatory ratio which is substantially similar to age- and sex-matched healthy subjects. As used herein, the conditioned blood refers to physical components present in the blood (or fraction thereof, such as the plasma) obtained by administering the first leukocyte to the immune competent test subject and having the pro-tolerogenic properties described herein. It is recognized by those skilled in the art that the conditioned blood may be obtained more rapidly by increasing the amount of leukocytes being administered or administering more than once (for example one, twice or thrice) the first leukocyte. Usually, the conditioned blood is obtained at least one day after the administration of the first leukocyte. In some embodiment, the conditioned blood is obtained at least 2, 3, 4, 5, 6 or 7 days after the administration of the first leukocyte. In an embodiment, the conditioned blood can be obtained by administering at least $5 \times 10^6$ allogeneic leukocytes to the test subject (e.g. a mice) and recuperating the plasma five days later. In some embodiments, the conditioned blood can be obtained by administering at least $20 \times 10^6$ allogeneic leukocytes.

As indicated herein, the two leukocyte populations are considered allogeneic (and in some embodiments, xenogeneic). When the acellular preparation is obtained in vivo by, for example, obtaining a conditioned blood/blood fraction by administering the first leukocyte to the test subject, the first leukocyte can be allogeneic or xenogeneic to the test subject. In such embodiment, it is also contemplated that the first leukocyte be autologous, syngeneic, allogeneic or xenogeneic to a treated subject who is going to receive the acellular preparation. When the acellular preparation is obtained in vitro by, for example, obtaining a conditioned medium by co-culturing the first leukocyte with the second leukocyte, the first leukocyte can be allogeneic or xenogeneic to the second leukocyte. In such embodiment, it is also contemplated that the first leukocyte be autologous, syngeneic, allogeneic or xenogeneic to a treated subject who is going to receive the acellular preparation. In addition, it is also contemplated that the second leukocyte be autologous, syngeneic, allogeneic or xenogeneic to a treated subject who is going to receive the acellular preparation.

Once the conditioned medium or the conditioned blood has been obtained it can be further processed to substantially remove the cells and cellular debris that can be present. This processing step can be achieved by submitting the conditioned medium or the conditioned blood to a centrifugation step and/or a filtration step. For example, blood can be processed to as to obtain the plasma. Since the majority of the immuno-modulatory effects of the acellular preparations reside in a fraction sensitive to ribonucleic acid degradation (e.g. RNase degradation), this process step should be conducted in conditions which would substantially limit or even inhibit ribonucleic acid degradation.

The conditioned medium or the conditioned blood can also processed (preferably after the removal of cells/cellular debris) so as to provide an enrichment in at least one miRNA species, and preferably a plurality of miRNA species. As used in the context of this invention, the term "enrichment" refers to the step of increasing the concentration of one or more miRNA species in the acellular preparation when compared to conditioned medium/blood. In an embodiment, the term enrichment refers to the step of increasing, in the acellular preparation, the concentration but not the relative abundance of the miRNA species present in the conditioned medium/blood. In still another embodiment, the enrichment step can comprises substantially isolating the miRNA species from other components that may be present the conditioned medium/blood (e.g. proteins such as cytokines for example). This enrichment step can be completed using various methods known to those skilled in the art, for example, chromatography, precipitation, etc. Since most of the immuno-modulatory effects of the acellular preparations reside in a fraction sensitive to ribonucleic acid degradation (e.g. RNase degradation), this process step should be conducted in conditions which would substantially limit or even inhibit ribonucleic acid degradation.

The conditioned medium or the conditioned blood can also be processed to substantially remove the protein components (including the cytokines) and/or the deoxyribonucleic acid components that may be present. Such further purification step can be made, for example, by using proteinase (to provide a protein-free acellular preparation), DNAse (to provide a DNA-free acellular preparation), chromatography or filtration (to provide a fraction enriched in size-specific components present in the conditioned medium/blood).

In some embodiments, it is also contemplated that the acellular preparation be submitted to the selective enrichment in components of the conditioned medium/blood having a relative size equal to or lower than about 20 kDa, 19 kDa, 18 kDa, 17 kDa, 16 kDa, 15 kDa, 14 kDa, 13 kDa, 12 kDa, 11 kDa, 10 kDa, 9 kDa, 8 kDa, 7 kDa, 6 kDa, 5 kDa, 4 kDa or 3 kDa.

Once the acellular preparation has been obtained, it can be formulated for administration to the subject. The formulation step can comprise admixing the acellular preparation with pharmaceutically acceptable diluents, preservatives, solubilizers, emulsifiers, and/or carriers. The formulations are preferably in a liquid injectable form and can include diluents of various buffer content (e.g., Tris-HCl, acetate, phosphate), pH and ionic strength, additives such as albumin or gelatin to prevent absorption to surfaces. The formulations can comprise pharmaceutically acceptable solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol).

In addition, if the acellular preparation is destined to be used to prevent, treat or alleviate the symptoms of cancer, it can be formulated to be co-administered with an anti-neoplastic agent. The acellular preparation can be formulated for simultaneous administration with the anti-neoplastic agent by admixing the anti-neoplastic agent with the acellular preparation. Alternatively, the acellular preparation can be formulated for administration prior to or after the anti-neoplastic agent, for example in a formulation that is physically distinct from the anti-neoplastic agent.

In another embodiment, if the acellular preparation is destined to be used to prevent, treat or alleviate the symptoms of an infection, it can be formulated to be co-administered with an anti-infective agent (such as an anti-parasitic, antibacterial, anti-viral or anti-fungal agent). The acellular preparation can be formulated for simultaneous administration with the anti-infective agent by admixing the anti-infective agent with the acellular preparation. Alternatively, the acellular preparation can be formulated for administration prior to or after the anti-infective agent, for example in a formulation that is physically distinct from the anti-infective agent.

Characterization of the miRNA Fraction of the Acellular Preparation

As shown herein, the miRNA fraction of the acellular preparation is associated with the majority of the pro-inflammatory immunomodulatory effects of the conditioned medium/blood. As also shown herein, the pro-inflammatory immunomodulatory effects of the miRNA fraction of the acellular preparation are greatly reduced (and even abolished) when the components of the conditioned blood/medium having an average molecular weight lower than about 10 kDa are removed or upon treatment with a ribonucleic acid degradation agent (such as RNase A).

The acellular preparation described herein does comprise a plurality (also referred to a population) of distinct miRNA species whose relative abundance differs from a control medium obtained from a mPEG MLR (e.g. in which two allogeneic leukocyte populations are co-cultured under conditions so as to allow pro-tolerogenic allo-recognition) or a control blood obtained from administering polymer-modified (PEGylated) allogeneic leukocytes (capable of allowing a pro-tolerogenic allo-recognition) to a test subject. The acellular preparation described herein also comprise a plurality (also referred to as a population) of distinct miRNA species whose relative abundance differs from a conditioned medium obtained from resting cells (e.g. a single cultured leukocyte population) or a blood obtained from a naïve test subject. This modulation in the relative abundance of the various miRNA species of the acellular preparation is believed to be tied to its pro-inflammatory immunomodulatory effects. The increased abundance of single miRNA species, unchanged abundance of single miRNA species and/or decreased abundance of single miRNA species are believed to contribute to the pro-inflammatory immunomodulatory effects of the acellular preparation. In an embodiment, in the acellular preparation, the relative pattern of expression of the miRNA species present when compared to the corresponding in the conditioned medium/blood obtained from using polymer-modified leukocytes (capable of allowing pro-tolerogenic allo-recognition) or medium from resting cells/naïve blood is conserved.

In an embodiment, the acellular preparation comprises at least one miRNA species presented in FIG. 9. In another embodiment, the acellular preparation comprises any combination of at least 2, 3, 4, 5, 10, 15, 20, 25, 30, 30, 35, 40, 45, 50, 55, 60, 65, 70, 75 or 80 of the miRNA species presented in FIG. 9. In still another embodiment, the acellular preparation comprises all the miRNA species presented in FIG. 9. FIG. 9 provides the following miRNA species: hsa-let-7a-5p, hsa-let-7c, hsa-let-7d-5p, hsa-let-7e-5p, hsa-let-7g-5p, hsa-miR-103a-3p, hsa-miR-105-5p, hsa-miR-125a-5p, hsa-miR-125b-5p, hsa-miR-126-3p, hsa-miR-128, hsa-miR-130a-3p, hsa-miR-132-3p, hsa-miR-134, hsa-miR-135a-5p, hsa-miR-135b-5p, hsa-miR-138-5p, hsa-miR-142-3p, hsa-miR-142-5p, hsa-miR-143-3p, hsa-miR-145-5p, hsa-miR-146a-5p, hsa-miR-147a, hsa-miR-148a-3p, hsa-miR-149-5p, hsa-miR-150-5p, hsa-miR-152, hsa-miR-155-5p, hsa-miR-15a-5p, hsa-miR-15b-5p, hsa-miR-16-5p, hsa-miR-17-5p, hsa-miR-181a-5p, hsa-miR-182-5p, hsa-miR-183-5p, hsa-miR-184, hsa-miR-185-5p, hsa-miR-186-5p, hsa-miR-187-3p, hsa-miR-18a-5p, hsa-miR-18b-5p, hsa-miR-191-5p, hsa-miR-194-5p, hsa-miR-195-5p, hsa-miR-196a-5p, hsa-miR-19a-3p, hsa-miR-19b-3p, hsa-miR-200a-3p, hsa-miR-203a, hsa-miR-205-5p, hsa-miR-206, hsa-miR-20a-5p, hsa-miR-20b-5p, hsa-miR-21-5p, hsa-miR-210, hsa-miR-214-3p, hsa-miR-223-3p, hsa-miR-23b-3p, hsa-miR-26a-5p, hsa-miR-26b-5p, hsa-miR-27a-3p, hsa-miR-27b-3p, hsa-miR-298, hsa-miR-299-3p, hsa-miR-29b-3p, hsa-miR-29c-3p, hsa-miR-302a-3p, hsa-miR-30b-5p, hsa-miR-30c-5p, hsa-miR-30e-5p, hsa-miR-31-5p, hsa-miR-325, hsa-miR-335-5p, hsa-miR-34a-5p, hsa-miR-363-3p, hsa-miR-379-5p, hsa-miR-383, hsa-miR-409-3p, hsa-miR-451a, hsa-miR-493-3p, hsa-miR-574-3p, hsa-miR-9-5p, hsa-miR-98-5p and hsa-miR-99b-5p.

In another embodiment, the acellular preparation comprises at least one miRNA species whose relative abundance is increased when compared to a conditioned medium/blood obtained from using polymer-modified leukocytes (capable of allowing pro-tolerogenic allo-recognition) or resting cells/naïve blood. Such miRNA species are listed in Tables 1A to 1 D.

TABLE 1A miRNA species in which the relative abundance in the conditioned medium of the control MLR is increased when compared to the miRNA species's conditioned medium from resting cells/naïve blood (as determined in FIG. 9). miRNA species identified with an * show a log$_2$ fold regulation change or a p ≤ 0.05 on a volcano plot.

hsa-let-7c
hsa-miR-105-5p
hsa-miR-130a-3p
hsa-miR-134
hsa-miR-135a-5p
hsa-miR-135b-5p*
hsa-miR-142-3p
hsa-miR-142-5p
hsa-miR-147a*
hsa-miR-149-5p
hsa-miR-155-5p*
hsa-miR-15a-5p
hsa-miR-181a-5p
hsa-miR-183-5p*
hsa-miR-187-3p
hsa-miR-18a-5p
hsa-miR-18b-5p
hsa-miR-200a-3p
hsa-miR-203a*
hsa-miR-205-5p
hsa-miR-206*
hsa-miR-210
hsa-miR-214-3p*
hsa-miR-299-3p
hsa-miR-29b-3p
hsa-miR-302a-3p*
hsa-miR-31-5p
hsa-miR-325*
hsa-miR-363-3p*
hsa-miR-383
hsa-miR-451a
hsa-miR-493-3p
hsa-miR-574-3p
hsa-miR-9-5p*

In a further embodiment, the acellular preparation comprises at least one miRNA species listed Table 1A. In still a further embodiment, the acellular preparation comprises a combination of at least 2, 3, 4, 5, 10, 15, 20, 25, 30 or 33 of any one of the miRNA species listed in Table 1A. In yet a further embodiment, the acellular preparation comprises all the miRNA species listed in Table 1A.

In an embodiment, the acellular preparation comprises at least one (or any combination of) miRNA species listed in Table 1A and showing a log$_2$ fold regulation change or a p 0.05 on a volcano plot (e.g., hsa-miR-135b-5p, hsa-miR-147a, hsa-miR-155-5p, hsa-miR-183-5p, hsa-miR-203a, hsa-miR-206, hsa-miR-214-3p, hsa-miR-302a-3p, hsa-miR-325, hsa-miR-363-3p, hsa-miR-9-5p).

TABLE 1B miRNA species in which the relative abundance in the conditioned medium of control MRL is increased when compared to the miRNA species's abundance in the conditioned medium of the mPEG MRL and is decreased when compared the miRNA species' abundance in the medium from resting cells/naïve blood (as determined in FIG. 9). miRNA species identified with an * show a log$_2$ fold regulation change or a p ≤ 0.05 on a volcano plot.

hsa-miR-183-5p*
hsa-miR-203a*
hsa-miR-363-3p*

In a further embodiment, the acellular preparation comprises at least one miRNA species listed Table 1B. In still a further embodiment, the acellular preparation comprises a combination of at least 2 of any one of the miRNA species listed in Table 1B. In yet a further embodiment, the acellular preparation comprises all the miRNA species listed in Table 1B.

TABLE 1C miRNA species in which the relative abundance in the conditioned medium of the control MLR is increased when compared to miRNA species's abundance in the conditioned medium of the resting cells/naïve blood. The relative abundance of these miRNA species is also increased in the conditioned medium of the mPEG MLR when compared to miRNA species's abundance in the conditioned medium of the resting cells/naïve blood (as determined in FIG. 9). miRNA species identified with an * show a log$_2$ fold regulation change or a p ≤ 0.05 on a volcano plot.

hsa-let-7c
hsa-miR-105-5p
hsa-miR-130a-3p
hsa-miR-134
hsa-miR-135a-5p
hsa-miR-135b-5p*
hsa-miR-142-3p
hsa-miR-142-5p
hsa-miR-147a*
hsa-miR-149-5p*
hsa-miR-155-5p*
hsa-miR-15a-5p
hsa-miR-181a-5p
hsa-miR-187-3p
hsa-miR-18a-5p
hsa-miR-18b-5p
hsa-miR-200a-3p
hsa-miR-205-5p
hsa-miR-206*
hsa-miR-210
hsa-miR-214-3p*
hsa-miR-299-3p
hsa-miR-29b-3p
hsa-miR-302a-3p*
hsa-miR-31-5p
hsa-miR-383
hsa-miR-451a
hsa-miR-493-3p
hsa-miR-574-3p
hsa-miR-9-5p*

In a further embodiment, the acellular preparation comprises at least one miRNA species listed Table 1C. In still a further embodiment, the acellular preparation comprises a combination of at least 2, 3, 4, 5, 10, 15, 20, 25 or 30 of any one of miRNA species listed in Table 1C. In yet a further embodiment, the acellular preparation comprises all the miRNA species listed in Table 1C.

In an embodiment, the acellular preparation comprises at least one (or any combination of) miRNA species listed in Table 1C and showing a log$_2$ fold regulation change or a p 0.05 on a volcano plot (e.g., hsa-miR-135b-5p, hsa-miR-147a, hsa-miR-149-5p, hsa-miR-155-5p, hsa-miR-206, hsa-miR-214-3p, hsa-miR-302a-3p and/or hsa-miR-9-5p). In an embodiment, the acellular preparation comprises at least one of hsa-mir-147a and hsa-mir-9-5p.

TABLE 1D

Selection of the miRNA species from Table 1C which show an increase of a log$_2$ fold regulation change or a p ≤ 0.05 on a volcano plot.

hsa-miR-135b-5p
hsa-miR-147a
hsa-miR-149-5p
hsa-miR-155-5p
hsa-miR-183-5p
hsa-miR-203a-5p
hsa-miR-206
hsa-miR-214-3p

TABLE 1D-continued

Selection of the miRNA species from Table 1C which show an increase of a log$_2$ fold regulation change or a p ≤ 0.05 on a volcano plot.

hsa-miR-302a-3p
hsa-miR-363-3p
hsa-miR-9-5p

In a further embodiment, the acellular preparation comprises at least one miRNA species listed Table 1D. In still a further embodiment, the acellular preparation comprises a combination of at least 2, 3, 4, 5, 6 or 7 of any one of miRNA species listed in Table 1D. In yet a further embodiment, the acellular preparation comprises all the miRNA species listed in Table 1D.

In another embodiment, the acellular preparation comprises at least one miRNA species whose relative abundance is decreased when compared to a conditioned medium/blood obtained from using polymer-modified leukocytes (capable of allowing pro-tolerogenic allo-recognition) or the medium fom resting cells/naïve blood. Such miRNA species are listed in Tables 2A to 2D.

TABLE 2A miRNA species in which the relative abundance in the conditioned medium of the control MLR is decreased when compared to the miRNA species's conditioned medium from resting cells/naïve blood (as determined in FIG. 9). miRNA species identified with an * show a log$_2$ fold regulation change or a p ≤ 0.05 on a volcano plot.

hsa-let-7a-5p*
Has-let-7d-5p
hsa-let-7e-5p*
hsa-let-7g-5p
hsa-miR-103a-3p
hsa-miR-125a-5p
hsa-miR-125b-5p
hsa-miR-126-3p
hsa-miR-128
hsa-miR-132-3p*
hsa-miR-138-5p
hsa-miR-143-3p
hsa-miR-145-5p
hsa-miR-146a-5p
hsa-miR-148a-3p
hsa-miR-150-5p
hsa-miR-152
hsa-miR-15b-5p
hsa-miR-16-5p
hsa-miR-17-5p
hsa-miR-182-5p
hsa-miR-184
hsa-miR-185-5p
hsa-miR-186-5p
has-miR-191-5p
hsa-miR-194-5p
hsa-miR-195-5p
hsa-miR-196a-5p
hsa-miR-19a-3p
hsa-miR-19b-3p
hsa-miR-20a-5p
hsa-miR-20b-5p
hsa-miR-21-5p*
hsa-miR-223-3p
hsa-miR-23b-3p
hsa-miR-26a-5p
hsa-miR-26b-5p
hsa-miR-27a-3p*
hsa-miR-27b-3p*
hsa-miR-298*
hsa-miR-29c-3p
hsa-miR-30b-5p
hsa-miR-30c-5p
hsa-miR-30e-5p

TABLE 2A-continued miRNA species in which the relative abundance in the conditioned medium of the control MLR is decreased when compared to the miRNA species's conditioned medium from resting cells/naïve blood (as determined in FIG. 9). miRNA species identified with an * show a log$_2$ fold regulation change or a p ≤ 0.05 on a volcano plot.

hsa-miR-335-5p
hsa-miR-34a-5p*
hsa-miR-379-5p
hsa-miR-409-3p
hsa-miR-98-5p
hsa-miR-99b-5p In a further embodiment, the acellular preparation comprises at least one miRNA species listed Table 2A. In still a further embodiment, the acellular preparation comprises a combination of at least 2, 3, 4, 5, 10, 15, 20, 25, 30, 35, 40, 45 or 46 of any one of miRNA species listed in Table 2A. In yet a further embodiment, the acellular preparation comprises all the miRNA species listed in Table 2A.

In an embodiment, the acellular preparation comprises at least one (or any combination of) miRNA species listed in Table 2A and showing a log$_2$ fold regulation change or a p 0.05 on a volcano plot (e.g., hsa-let-7a-5p, hsa-let-7e-5p, hsa-miR-132-3p, hsa-miR-21-5p, hsa-miR-27a-3p, hsa-miR-27b-3p, hsa-miR-298, hsa-miR-34a-5p).

TABLE 2B miRNA species in which the relative abundance in the conditioned medium of control MRL is decreased when compared to the miRNA species's abundance in the conditioned medium of the mPEG MRL (as determined in FIG. 9). miRNA species identified with an * show a log$_2$ fold regulation change.

hsa-let-7a-5p*
hsa-let-7e-5p*
hsa-miR-132-3p*
hsa-miR-21-5p*
hsa-miR-27a-3p*
hsa-miR-27b-3p*
hsa-miR-298*
hsa-miR-34a-5p*

In a further embodiment, the acellular preparation comprises at least one miRNA species listed Table 2B. In still a further embodiment, the acellular preparation comprises a combination of at least 2, 3, 4, 5, 6 or 7 of any one of the miRNA species listed in Table 2B. In yet a further embodiment, the acellular preparation comprises all the miRNA species listed in Table 2B.

TABLE 2C

Selection of the miRNA species from Table 2B which show a log$_2$ fold regulation change or a p ≤ 0.05 on a volcano plot.

hsa-let-7a-5p
hsa-let-7e-5p
hsa-miR-132-3p
hsa-miR-21-5p
hsa-miR-27a-3p
hsa-miR-27b-3p
hsa-miR-298
hsa-miR-34a-5p In a further embodiment, the acellular preparation comprises at least one miRNA species listed Table 2C. In still a further embodiment, the acellular preparation comprises a combination of at least 2, 3, 4, 5, 6 or 7 any one of miRNA species listed in Table 2C. In yet a further embodiment, the acellular preparation comprises all the miRNA species listed in Table 2C.

TABLE 2D miRNA species in which the relative abundance in the conditioned medium of control MRL and in the condition medium of the mPRG MLR is decreased when compared to the miRNA species's abundance in the conditioned medium from resting cells/naïve blood (as determined in FIG. 9).

hsa-let-7d-5p
hsa-let-7g-5p
hsa-miR-103a-3p
hsa-miR-125a-5p
hsa-miR-125b-5p
hsa-miR-126-3p
hsa-miR-128
hsa-miR-138-5p
hsa-miR-143-3p
hsa-miR-145-5p
hsa-miR-146a-5p
hsa-miR-148a-3p
hsa-miR-150-5p
hsa-miR-152
hsa-miR-15b-5p
hsa-miR-16-5p
hsa-miR-17-5p
hsa-miR-182-5p
hsa-miR-184
hsa-miR-185-5p
hsa-miR-186-5p
has-miR-191-5p
hsa-miR-194-5p
hsa-miR-195-5p
hsa-miR-196a-5p
hsa-miR-19a-3p
hsa-miR-19b-3p
hsa-miR-20a-5p
hsa-miR-20b-5p
hsa-miR-223-3p
hsa-miR-23b-3p
hsa-miR-26a-5p
hsa-miR-26b-5p
hsa-miR-29c-3p
hsa-miR-30b-5p
hsa-miR-30c-5p
hsa-miR-30e-5p
hsa-miR-335-5p
hsa-miR-379-5p
hsa-miR-409-3p
hsa-miR-98-5p
hsa-miR-99b-5p In a further embodiment, the acellular preparation comprises at least one miRNA species listed Table 2D. In still a further embodiment, the acellular preparation comprises a combination of at least 2, 3, 4, 5, 10, 15, 20, 25, 30, 35, 40 or 42 of any one of miRNA species listed in Table 2D. In yet a further embodiment, the acellular preparation comprises all the miRNA species listed in Table 2D.

It is contemplated that the acellular preparation comprises at least one (and in an embodiment any combination of) miRNAs species from any one of Tables 1A to 1D and at least one (and in an embodiment any combination of) miRNAs species from any one of Tables 2A to 2D.

Figure 8B:
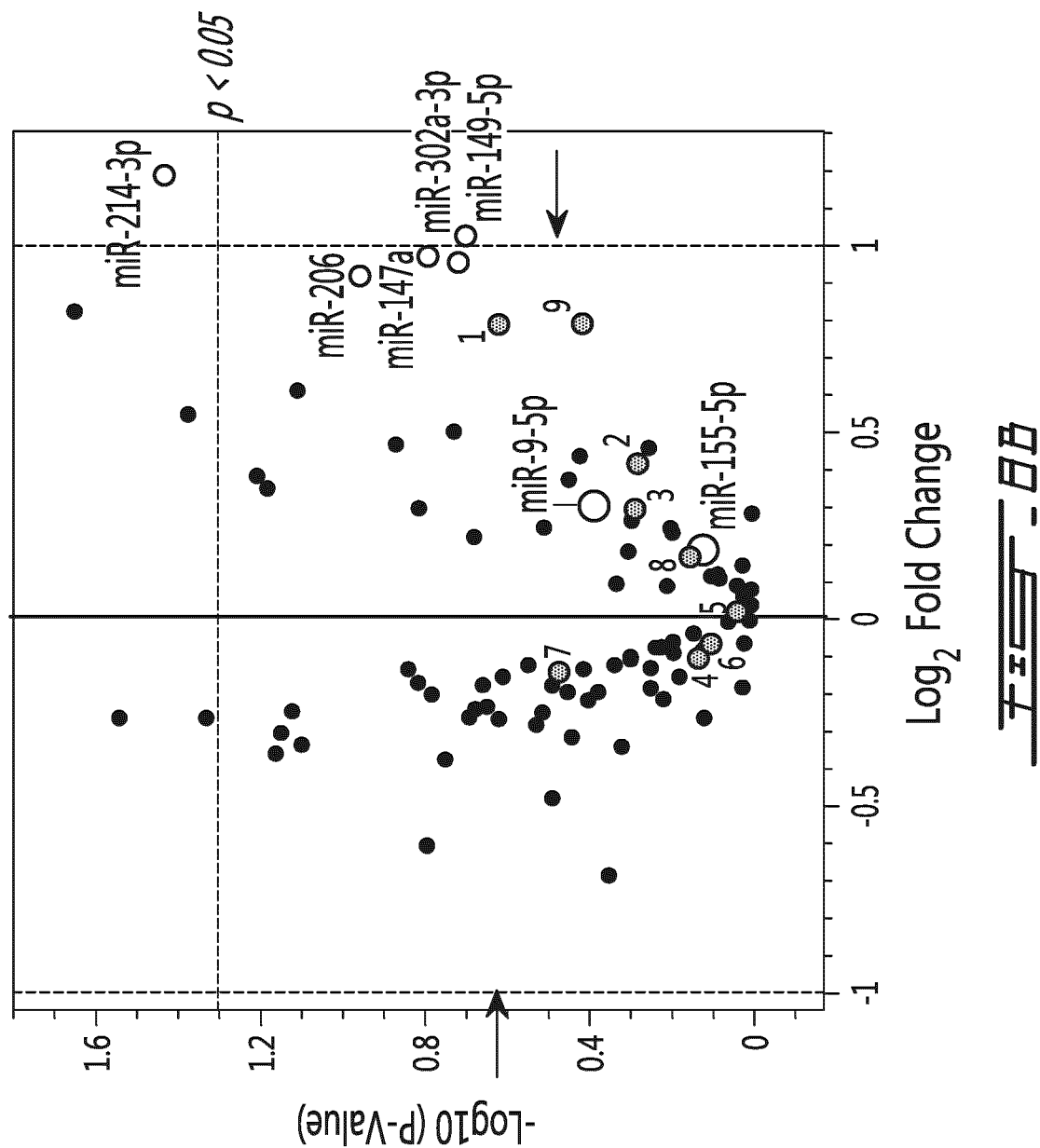
FIG. 8 provides a comparison of the miRNA populations between different MLR assays. A human PBMC MLR assay (using unmodified (control MLR) or polymer modified leukocyte (mPEG MLR)) was conducted and miRNA content was partially determined. Volcano plots of comparing the miRNA population of the conditioned medium of the control MLR to the one of the supernatant of resting cells (A), comparing the miRNA population of the conditioned medium of a mPEG MLR to the one of the supernatant of resting cells (B) and comparing the miRNA population of the conditioned medium of a mPEG MLR to the one of the conditioned medium of a control MLR (C) are provided. Results are provided in $-Log_{10}$ (p value) in function of $Log_2$ fold change. In these volcano plots, the following miRNAs have been identified with numbers.

In yet another embodiment, the acellular preparation can comprise at least one of the miRNA species identified in the volcano plots of FIG. 8. In still another embodiment, the acellular preparation comprises at least one (or any combination of) miRNA species presented on FIG. 8A which exhibits at least a $\log_2$ fold modulation in abundance (e.g. miR-302a-3p, miR214-3p, miR-147a, miR206, miR 155-5p and/or miR-9-5p). In yet still another embodiment, the acellular preparation comprises at least one (or any combination of) of miRNA species presented on FIG. 8A which exhibits at least $p \leq 0.05$ (e.g. miR214-3p, miR-147a, miR206, miR 155-5p and/or miR-9-5p). In yet another embodiment, the acellular preparation comprises at least one (or any combination of) miRNA species presented on FIG. 8B which exhibits at least a $\log_2$ fold modulation in abundance (e.g. miR-149-5p and/or miR-214-3p). In yet still another embodiment, the acellular preparation comprises the miRNA species presented on FIG. 8B which exhibits at least $p \leq 0.05$ (e.g. miR-214-3p). In yet another embodiment, the acellular preparation comprises at least one (or any combination of) miRNA species presented on FIG. 8C which exhibits at least a $\log_2$ fold modulation in abundance (e.g. miR-147a, miR-183-5p, miR-9-5p and/or miR-155-5p). In yet still another embodiment, the acellular preparation comprises at least one (or any combination of) miRNA species presented on FIG. 8C which exhibits at least $p \leq 0.05$ (e.g. miR-9-5p and/or miR-155-5p).

It is contemplated that the acellular preparation comprises at least one (and in an embodiment any combination of) miRNAs species from any one of Tables 1A to 1D, at least one (and in an embodiment any combination of) miRNAs species from any one of Tables 2A to 2D and at least one (and in an embodiment any combination of) miRNA species identified in any one of the FIG. 8A to 8C.

Methods for Modulating the Treg/Pro-Inflammatory T Cells Ratio

The present invention provides methods and acellular preparations for decreasing the ratio of the level of regulatory T cells with respect to the level of pro-inflammatory T cells. In the present invention, the ratio can be decreased either by lowering the level of regulatory T cells in the subject or increasing the level of pro-inflammatory T cells in the subject. Alternatively, the ratio can be decreased by lowering the level of regulatory T cells in the subject and increasing the level of pro-inflammatory T cells in the subject. When the Treg/pro-inflammatory T cells ratio is decreased in a subject, it is considered that a state of immune stimulation is induced or present in the subject. The induction of a state of immune stimulation in subjects experiencing an abnormally decreased immune state can be therapeutically beneficial for limiting the symptoms or pathology associated with the abnormally low immune reaction or an acquired state of anergy. In some embodiments, it is not necessary to induce a state of complete immune stimulation, a partial induction of immune stimulation can be beneficial to prevent, treat and/or alleviate the symptoms of a disorder associated with a pro-tolerogenic state (such as, for example, a proliferation-associated disorder or an infection).

In order to decrease the Treg/pro-inflammatory T cells ratio, an allogeneic acellular preparation can be administered to the subject in a therapeutically effective amount. In such instances, the acellular preparation obtained by the process described above or characterized above can be used.

An alternative way of decreasing the Treg/pro-inflammatory Tcell ratio in a subject to be treated, is to administer the conditioned blood (or fraction thereof such as plasma or serum) of a test subject that has been administered with a first non-proliferative allogeneic leukocyte. The animal is transfused in conditions so as to allow a pro-inflammatory allo-recognition but to prevent the onset of GVHD. The first leukocyte is considered immunogenic (e.g. allogeneic) with respect to the test subject because when the first leukocyte is transfused into the animal, an immune response (e.g. a cell-mediated immune response, preferably a pro-inflammatory allo-recognition) occurs. In another embodiment, the first leukocyte can be xenogeneic with respect to the animal.

However, the first leukocyte cannot be autologous or syngeneic to the animal. In some embodiments, the first leukocyte can be allogeneic or xenogeneic to the subject which will be treated with the conditioned blood. In alternative embodiment, the first leukocyte can be syngeneic or derived from the subject which will be treated with the conditioned blood. In an embodiment, the first allogeneic leukocyte can be modified to bear on its surface a polymer. However, the polymer, when present, must be selected or grafted at a density so as to allow the pro-inflammatory allo-recognition of the first leukocyte by the recipient. When the first leukocyte is modified to bear on its surface a polymer, it can be modified to be non-proliferative either prior to or after the polymer modification.

As shown herein, the administration of the acellular preparations induce a state of immune stimulation in the treated subject. In some embodiments, the state of stimulation can persist long after the administration of the acellular preparations (as shown below, at least 270 days in mice). In an optional embodiment, the state of stimulation does not revert back to a pro-tolerogenic state. Consequently, the methods and acellular preparations described herein are useful for the treatment, prevention and/or alleviation of symptoms associated with conditions caused/exacerbated by a low or inappropriate immune response.

A state of immune stimulation can be considered therapeutically beneficial in subjects experiencing a repressed immune response (anergy or tolerance), such as for example those observed upon the induction and maintenance of an proliferation-associated disorder (such as cancer). Some of these conditions are associated with either a high level of Tregs and/or a low level of pro-inflammatory T cells (such as Th17 and/or Th1) when compared to sex- and aged-matched healthy subjects. Because it is shown herein that the acellular-based preparations are beneficial for decreasing the ratio Tregs/pro-inflammatory T cells, it is expected that administration of the acellular-based preparations to afflicted subjects will treat, prevent and/or alleviate symptoms associated with the proliferation-associated disorder.

A state of immune stimulation can also be considered therapeutically beneficial in subjects at risk of developing an abnormally repressed immune response, a state or anergy or a pro-tolerogenic state. Such abnormally repressed immune responses can be observed in subjects being afflicted by or susceptible to be afflicted by a proliferation-associated disorder such as cancer. In some embodiments, the acellular preparations are used for the treatment, prevention and/or alleviations of symptoms of non-blood cancer (e.g. solid cancers), such as, for example, carcinoma, melanoma, sarcoma, bastoma and germ-cell tumors. In this embodiment, the methods and acellular preparations can be applied to prevent or limit the onset or maintenance of a repressed immune response. The acellular-based preparation can be co-administered with the other therapeutics currently used to managed the proliferation-associated disorder. The acellular-based preparation can be administered to any subjects in need thereof, including humans and animals.

Such abnormally repressed immune responses can be also observed in subjects being infected, especially by a parasite or a virus. In these conditions, the methods and acellular preparations can be applied to prevent or limit the onset or maintenance of a repressed immune response. The acellular-based preparation can be co-administered with the other therapeutics currently used to managed the infection.

The acellular-based preparation can be administered to any subjects in need thereof, including humans and animals.

In an embodiment, the state of abnormal repression of the immune system is not caused by an infection of the immune cells themselves (e.g. EBV or HIV for example). However, in other embodiment, in instances where an infection of the immune cells is afflicting the subject, it is possible to use acellular preparations described to treat or alleviate the symptoms of the viral infection. For example, a leukocyte from the subject (preferably a cytotoxic T cell which is specific to the infectious agent) can be co-cultured with the acellular preparations described herein. After the co-culture, the cultured leukocyte can be reintroduced in the infected subject to treat and/or alleviate the symptoms associated to the infection (a viral infection, for example, an EBV or HIV infection). In another example, the acellular preparations described herein can be administered to the infected individual to provide immune stimulation.

In the methods and acellular preparations described herein, it is contemplated that the acellular-based preparations be optionally administered with other therapeutic agents known to be useful for the treatment, prevention and/or alleviation of symptoms of conditions associated to a condition caused/exacerbated by a low or inappropriate immune response, such as, for example, IL-2, IL-4, TNF-α and/or INF-γ.

The present invention will be more readily understood by referring to the following examples which are given to illustrate the invention rather than to limit its scope.

Example I

Material and Methods

Human PBMC and Dendritic Cell Preparation.

Human whole blood was collected in heparinized vacutainer blood collection tubes (BD, Franklin Lakes, N.J.) from healthy volunteer donors following informed consent. PBMC were isolated from diluted whole blood using Ficol-lePaque PREMIUM™ (GE Healthcare Bio-Sciences Corp, Piscataway, N.J.) as per the product instructions. The PBMC layer was washed twice with 1× Hank's Balanced Salt Solution (HBSS; without $CaCl_2$ and $MgSO_4$; Invitrogen by Life Technologies, Carlsbad, Calif.) and resuspended in the appropriate media as needed for mixed lymphocyte reactions and flow cytometric analysis of Treg and Th17 phenotypes. Dendritic cells (DC) were prepared from isolated PBMC as described by O'Neill and Bhardwaj (O'Neill et al., 2005). Briefly, freshly isolated PBMC were overlaid on Petri dishes for 3 h in AIM V serum free culture medium (Invitrogen, Carlsbad, Calif.). Non-adherent cells were gently washed off the plate. The adherent cells (monocyte rich cells) were treated with IL-4 and GM-CSF (50 and 100 ng/mL respectively; R&D Systems, Minneapolis, Minn.) in AIM V medium. Cells were again treated with IL-4 and GM-CSF on days 2 and 5. On day 6, cells were centrifuged and resuspended in fresh media supplemented with DC maturation factors (TNF-α, IL-1β, IL-6; R&D Systems, Minneapolis, Minn.) and prostaglandin E2 (Sigma Aldrich, St. Louis, Mo.). The mature DC-like cells were harvested on day 7 and CD80, CD83, CD86 and HLA-DR expressions were determined to confirm DC maturation via flow cytometry (FACSCalibur™ Flow Cytometer, BD Biosciences, San Jose, Calif.).

Murine Splenocyte and Tissue Harvesting.

All murine studies were done in accordance with the Canadian Council of Animal Care and the University of British Columbia Animal Care Committee guidelines and were conducted within the Centre for Disease Modeling at the University of British Columbia. Murine donor cells used for the in vivo donation and in vitro studies were euthanized by $CO_2$. Three allogeneic strains of mice were utilized for syngeneic and allogeneic in vitro and in vivo challenge: Balb/c, $H-2^d$; C57Bl/6, $H-2^b$; and C3H, $H-2^k$. Murine spleens, brachial lymph nodes, and peripheral blood were collected at the indicated days. Mouse spleens and brachial lymph nodes were dissected and placed into cold phosphate buffered saline (PBS; 1.9 mM $NaH_2PO_4$, 8.1 mM $Na_2HPO_4$, and 154 mM NaCl, pH 7.3) containing 0.2% bovine serum albumin (BSA; Sigma Aldrich, St. Louis, Mo.) and kept on ice until ready to process. Whole blood was collected in heparinized tubes via cardiac puncture. Murine donor splenocytes were prepared from freshly harvested syngeneic or allogeneic spleens via homogenization into a cell suspension in PBS (0.2% BSA) using the frosted end of two microscope slides. The resultant cell suspension was spun down at 500×g. The splenocyte pellet was resuspended in 1 mL of 1×BD Pharm LYSE™ lysing buffer (BD Biosciences, San Diego, Calif.) and incubated for 1 min at room temperature. Lymph node cells were harvested via tissue homogenization as described above, washed twice and resuspended in PBS (0.2% BSA) for flow cytometric analysis of Th17, Treg and murine haplotype. Recipient peripheral blood lymphocytes were prepared via lysis of the red cells (BD Pharm Lyse lysing buffer; BD Biosciences, San Diego, Calif.) at 1× concentration, followed by washing (1×) and resuspension in PBS (0.2% BSA) for flow analysis of Th17, Treg and murine haplotype.

mPEG Modification (PEGylation) of PBMCs and Splenocytes.

Human PBMC and murine splenocytes were derivatized using methoxypoly(-ethylene glycol) succinimidyl valerate (mPEG-SVA; Laysan Bio Inc. Arab, Ala.) with a molecular weight of 5 or 20 kDa as previously described (Scott et al., 1997; Murad et al, 1999; Chen et al., 2003; Chen et al., 2006). Grafting concentrations ranged from 0 to 5.0 mM per $4 \times 10^6$ cells/mL. Cells were incubated with the activated mPEG for 60 min at room temperature in isotonic alkaline phosphate buffer (50 mM $K_2HPO_4$ and 105 mM NaCl; pH 8.0), then washed twice with 25 mM HEPES/RPMI 1640 containing 0.01% human albumin. Human PBMC were resuspended in AIM V media at a final cell density of $2.0 \times 10^6$ cells/mL for use in the MLR. Murine splenocytes used for in vivo studies were resuspended in sterile saline at a final cell density of $2.0 \times 10^8$ cells/ml for i.v. injection. To determine if the simple presence of the mPEG polymer itself altered the immune response either in vitro and in vivo, additional studies were done with unactivated polymer incapable of covalent grafting to the cell surface. For these studies, allogeneic human (in vitro studies) or syngeneic and allogeneic murine splenocytes (in vivo studies) were treated with non-covalently bound mPEG (soluble mPEG) under the same reaction conditions described for the covalent grafting studies. For clarity, "soluble mPEG" refers to cells treated with non-covalently grafted polymer while "mPEG-modified" refers to treatment with activated polymer resulting in the covalent grafting of the mPEG to the cell membrane.

In Vitro and In Vivo Cell Proliferation.

Cell proliferation (both in vitro and in vivo) was assessed via flow cytometry using the CELLTRACE™ CFSE (Carboxyfluorescein diacetate, succinimidyl ester) Cell Proliferation Kit (Invitrogen by Life Technologies e Molecular probes, Carlsbad, Calif.). Human and murine cells labeling was done according to the product insert at a final concentration of 2.5 mM CFSE per $2 \times 10^6$ cells total. Donor and recipient cell proliferation was differentially determined by haplotype analysis. In some experiments, cell proliferation was measured by $^3$H-thymidine incorporation. In these experiments, donor splenocytes ($5.12 \times 10^6$ cells per well) were co-incubated in triplicate in 96-well plates at 37° C., 5% $CO_2$ for 3 days. On day 3, all wells were pulsed with $^3$H-thymidine and incubated for 24 h at 37° C., 5% $CO_2$. Cellular DNA was collected on filter mats using a Skatron cell harvester (Suffolk, U.K.) and cellular proliferation was measured by $^3$H-thymidine incorporation.

Mixed Lymphocyte Reaction (MLR)—Control and Conditioned Media.

The immunodulatory effects of the various preparations were assayed using a MLR (Murad et al, 1999; Chen et al., 2003; Chen et al., 2006; Wang et al., 2011). For the human MLRs, PBMC from two MHC-disparate human donors were labeled with CFSE. For mice MLR, splenocytes from two H-2-disparate mice (Balb/c and C57Bl/6) were labeled with CFSE. Each MLR reaction well contained a total of $1 \times 10^6$ cells (single donor for resting or mitogen stimulation or equal numbers for disparate donors for MLR). Cells were plated in multiwell flat-bottom 24-well tissue culture plates (BD Biosciences, Discovery Labware, Bedford, Mass.). PBMC proliferation, cytokine secretion, as well as Treg and Th17 phenotyping was done. For flow cytometric analysis, the harvested cells were resuspended in PBS (0.1% BSA).

Immunophenotyping by Flow Cytometry.

The T lymphocytes populations (double positive for $CD3^+$ and $CD4^+$) in both the in vitro and in vivo studies were measured by flow cytometry using fluorescently labeled CD3 and CD4 monoclonal antibodies (BD Pharmingen, San Diego, Calif.). Human and mouse Regulatory T lymphocytes (Treg) were $CD3^+/CD4^+$ and $FoxP3^+$ (transcription factor) while inflammatory Th17 lymphocytes cells were $CD3^+/CD4^+$ and $IL-17^+$ (cytokine) as measured per the BD Treg/Th17 Phenotyping Kit (BD Pharmingen, San Diego, Calif.). Additional cell surface markers were also used to characterize the cells or subsets of cells obtained: anti-CD69 (clone H1.2F3, BD Biosciences) and anti-CD25 (BD Biosciences). After the staining, the cells ($1 \times 10^6$ cells total) were washed and resuspended in PBS (0.1% BSA) prior to flow acquisition. Isotype controls were also used to determine background fluorescence. All samples were acquired using the FACSCalibur™ flow cytometer (BD Biosciences, San Jose, Calif.) and CellQuest Pro™ software for both acquisition and analysis.

Conditioned Plasma.

Mouse were either untreated (naïve) or treated with saline, non-polymer modified allogeneic splenocytes or PEGylated allogeneic splenocytes (obtained by the procedures explained above). After five days, a cell-free conditioned plasma was obtained (from mouse blood using the mirVana™ PARIS™ kit from Ambion by Life Technologies) and transfused to another naïve mouse.

Plasma Fractionation.

The plasma fractionation was performed using centrifugal filter molecular cutoff devices. Millipore's Amicon® Ultra-0.5 centrifugal filter devices were used (Amicon Ultra 3k, 10K, 30K, 50K, and 100K devices).

miRNA Extraction.

The miRNA was extracted from samples (conditioned medium or plasma) using mirVana™ PARIS™ kit from Ambion® by Life Technologies according to the manufacturer's instructions. Briefly, the sample is mixed with the 2× denaturing solution provided and subjected to acid-phenol: chloroform extraction. To isolate RNA that is highly enriched for small RNA species, 100% ethanol was added to bring the samples to 25% ethanol. When this lysate/ethanol mixture was passed through a glass-fiber filter, large RNAs are immobilized, and the small RNA species are collected in the filtrate. The ethanol concentration of the filtrate was then increased to 55%, and it was passed through a second glass-fiber filter where the small RNAs become immobilized. This RNA is washed a few times, and eluted in a low ionic strength solution. Using this approach, an RNA fraction highly enriched in RNA species <200 nt can be obtained. Note that the large RNA species (>200 nt) can be recovered from the first filter if necessary.

TA Preparations.

The murine miRNA preparations (e.g. TA1 preparations) used were extracted from the conditioned plasma obtained 5 days after mice have received mPEG allogeneic splenocytes. Extraction can occur at time points other than 5 days (e.g., 24 hours post administration) and yield similar results (data not shown). Five days was chosen as Treg levels achieved maximal levels at this point in the mice. The human miRNA preparations (e.g. TA2 preparations) used were extracted from the conditioned medium of an mPEG-MLR harvested 72 hours following the initiation of the mPEG-MLR. However, miRNA harvested from human PBMC mPEG-MLR at 24 hours also yields the desired immunomodulatory effects (data not shown). To calibrate, miRNA concentration can be quantitated via a Qubit® 2.0 Fluorometer (LifeTechnologies) and selected fluorescent dyes which emit a signal only when bound to specific target (i.e., miRNA) molecules.

IA Preparations.

The murine miRNA preparations (e.g. IA1 preparations) used were extracted from the conditioned plasma obtained 5 days after mice have received non-polymer modified allogeneic splenocytes. Extraction can occur at time points other than 5 days (e.g., 24 hours post administration) and yield similar results (data not shown). Five days was chosen as Th17 levels achieved maximal levels and Treg cells had reach their minimal level at this point in the mice. The human miRNA preparations (e.g. IA2 preparations) used were extracted from the conditioned medium of an mPEG-MLR harvested 72 hours following the initiation of the mPEG-MLR. However, miRNA harvested from human PBMC mPEG-MLR at 24 hours also yields the desired immunomodulatory effects (data not shown). To calibrate, miRNA concentration can be quantitated via a Qubit® 2.0 Fluorometer (LifeTechnologies) and selected fluorescent dyes which emit a signal only when bound to specific target (i.e., miRNA) molecules.

miRNA Characterization.

The miRNA of the conditioned medium were characterized by qPCR using the miScript miRNA™ PCR Array Human Immunopathology (Qiagen) for human conditioned medium and the Mouse Immunopathology miRNA PCR Array™ (Qiagen) for mouse conditioned plasma/media.

RNase Treatment.

Murine plasma was pooled and for each individual mouse. For each 500 µL of murine plasma (or the <10 kDa plasma fraction), 50 ng RNase (RNase A, 20 mg/mL stock, Life Technologies (In Vitrogen)) was added. Then samples were incubated for 10 minutes at 37° C. to degrade the nucleic acids. The control plasma (or <10 kDa fraction) without RNAase A treatment was incubated at 37° C. for 10 min. The RNase treated plasma (100 µl per mouse) was injected (i.v.) into mice (n=5). RNase A alone (10 ng/mouse) was used for the control mice to insure that the RNase A was not toxic and this trace amount of RNase did not have an in vivo immunomodulatory effects.

Phosphorylation of Phosphokinases.

Analyzing the phosphorylation state of kinases and their protein substrates allows for the characterization of the effects of conditioned plasma or media on how cells respond to allogeneic stimuli. The human phospho-kinase array (R&D Systems Inc) is a rapid, sensitive tool to simultaneously detect the relative levels of phosphorylation of 43 kinase phosphorylation sites and 2 related total proteins. Each capture antibody was carefully selected using cell lysates prepared from cell lines known to express the target protein. Capture and control antibodies are spotted in duplicate on nitrocellulose membranes. Cell lysates are diluted and incubated overnight with the human phospho-kinase array. The array is washed to remove unbound proteins followed by incubation with a cocktail of biotinylated detection antibodies. Streptavidin-HRP and chemiluminescent detection reagents are applied and a signal is produced at each capture spot corresponding to the amount of phosphorylated protein bound.

Statistical Analysis.

Data analysis for flow analysis was conducted using SPSS™ (v12) statistical software (Statistical Products and Services Solutions, Chicago, Ill., USA). For significance, a minimum p value of <0.05 was used. For comparison of three or more means, a one-way analysis of variance (ANOVA) was performed. When significant differences were found, a post-hoc Tukey test was used for pair-wise comparison of means. When only two means were compared, student-t tests were performed.

In Vivo Murine Studies.

Three genetically different strains: Balb/c, H-$2^d$; C57Bl/6, H-$2^b$; and C3H, H-$2^k$ (Chen et al., 2003; Chen et al., 2006). All mice (donors and recipients) were 9-11 weeks old. Donor splenocytes were prepared and CSFE labeled as described. control and mPEG-grafted (1 mM, 20 kDa SVAmPEG) syngeneic or allogeneic cells ($20 \times 10^6$ splenocytes) were transfused intravenously (i.v.) via the tail vein into recipient animals. BALB/c and C57BL/6 mice injected with sterile saline served as control animals. Animals were euthanized by $CO_2$ at predetermined intervals at which time blood, brachial lymph nodes and spleen were collected and processed for Th17/Treg phenotyping analysis and splenocyte proliferation studies by flow cytometry. Donor cell engraftment and proliferation were assessed via flow cytometry using murine haplotype (H-$2K^b$ vs. H-$2K^d$) analysis. To determine the persistence of the immunomodulation, mice were re-challenged (2° challenge) 30 days after the initial transfer of allogeneic or mPEGallogeneic splenocytes with unmodified allogeneic cells. At 5 days post 2° challenge, Treg and Th17 phenotyping of murine splenocytes isolated from the spleen, lymph node and peripheral blood was again assessed via flow cytometry.

Statistical Analysis.

Data analysis was conducted using SPSS™ (v12) statistical software (Statistical Products and Services Solutions, Chicago, Ill., USA). For significance, a minimum p value of <0.05 was used. For comparison of three or more means, a one-way analysis of variance (ANOVA) was performed. When significant differences were found, a post-hoc Tukey test was used for pair-wise comparison of means. When only two means were compared, student-t tests were performed.

Example II

Characterization of Conditioned Plasma Obtained from Administering Non-Polymer Grafted Lymphocytes The material and methods used in this example are provided in Example I.

Figure 1A:
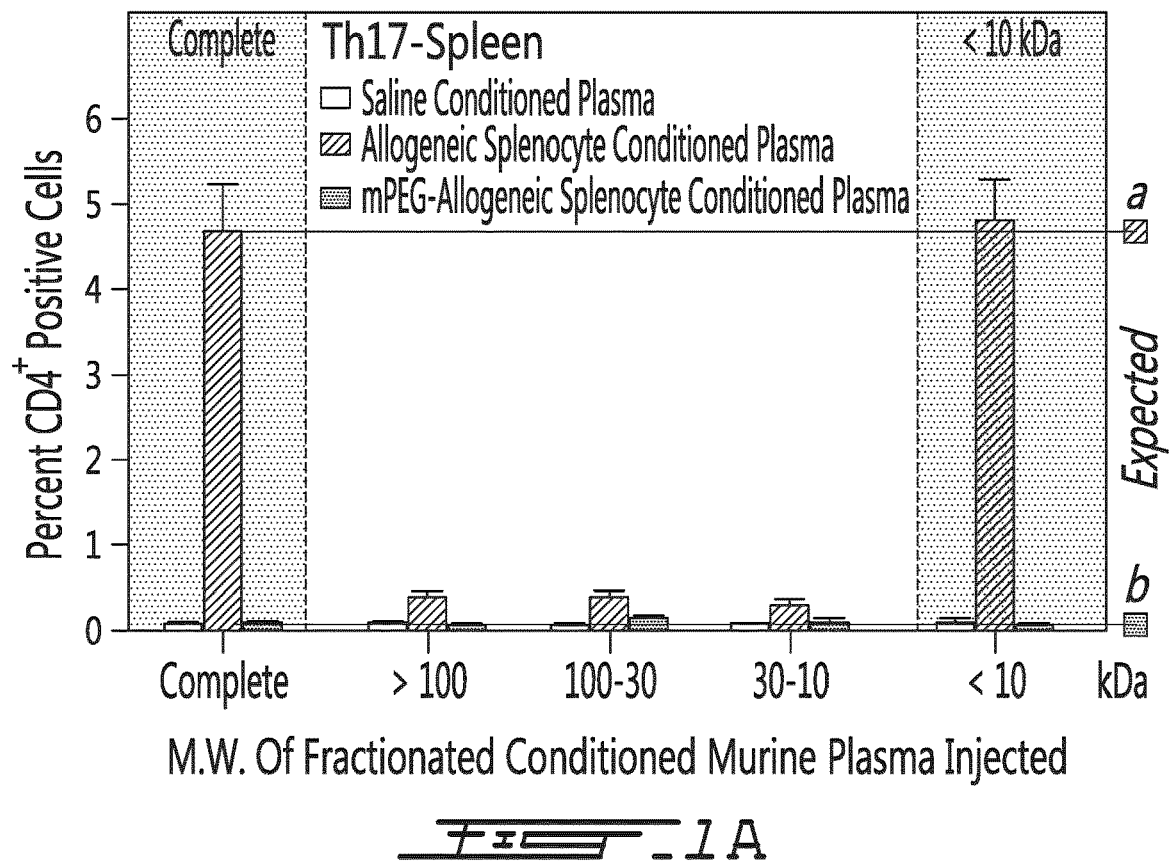
FIG. 1 illustrates the effects of size (MW) separation and RNase treatment on the immunomodulary effects of acellular preparations. Unmodified conditioned murine plasma (obtained from donor mice 5 days post splenocyte transfer), size fractionated-conditioned murine plasma or RNase-treated conditioned murine plasma was administered once to naïve mice and Treg/Th17 levels were measured (when) in the spleen. (A) Results are shown as the percentage of Th17 cells (in function of CD4$^+$ cells) in function of type of conditioned medium (white bars=conditioned plasma obtained from administering saline, hatched bars=conditioned plasma obtained from administering unmodified allogeneic splenocytes, grey bars=conditioned plasma obtained from administering polymer-modified allogeneic splenocytes) and size fractionation (non-fractioned or complete conditioned serum, fraction >100 kDa, fraction between 30 and 100 kDa, fraction between 10 and 30 kDa, fraction <10 kDa). a denotes the mean value for unfractionated conditioned medium prepared from mice previously treated with unmodified allogeneic cells. b denotes the mean value for unfractionated conditioned medium prepared from mice previously treated with mPEG-modified allogeneic cells. (B) Results are shown as the percentage of Treg cells (in function of CD4$^+$ cells) in function of type of conditioned medium (white bars=conditioned plasma obtained from administering saline, hatched bars=conditioned plasma obtained from administering unmodified allogeneic splenocytes, grey bars=conditioned plasma obtained from administering polymer-modified allogeneic splenocytes) and size fractionation (non-fractioned or complete conditioned serum, fraction >100 kDa, fraction between 30 and 100 kDa, fraction between 10 and 30 kDa, fraction <10 kDa). a denotes the mean value for unfractionated conditioned medium prepared from mice previously treated with unmodified allogeneic cells. b denotes the mean value for unfractionated conditioned medium prepared from mice previously treated with mPEG-modified allogeneic cells. (C) Results are shown as the percentage of Treg cells (in function of $CD4^+$ cells, left panel) or Th17 cells (in function of $CD4^+$ cells, right panel) in function of type of treatment (white bars=N=naïve untreated animals; grey bars=AC=unmodified allogeneic cells; diagonal hatch bars=conditioned plasma obtained from administered unmodified splenocytes treated (allo-plasma (+)) or not (allo-plasma (−)) with RNase; horizontal hatch bars=conditioned plasma obtained from administering polymer modified splenocytes treated (mPEG-allo-plasma (+)) or not (mPEG-allo-plasma (−)) with RNase).
Figure 1B:
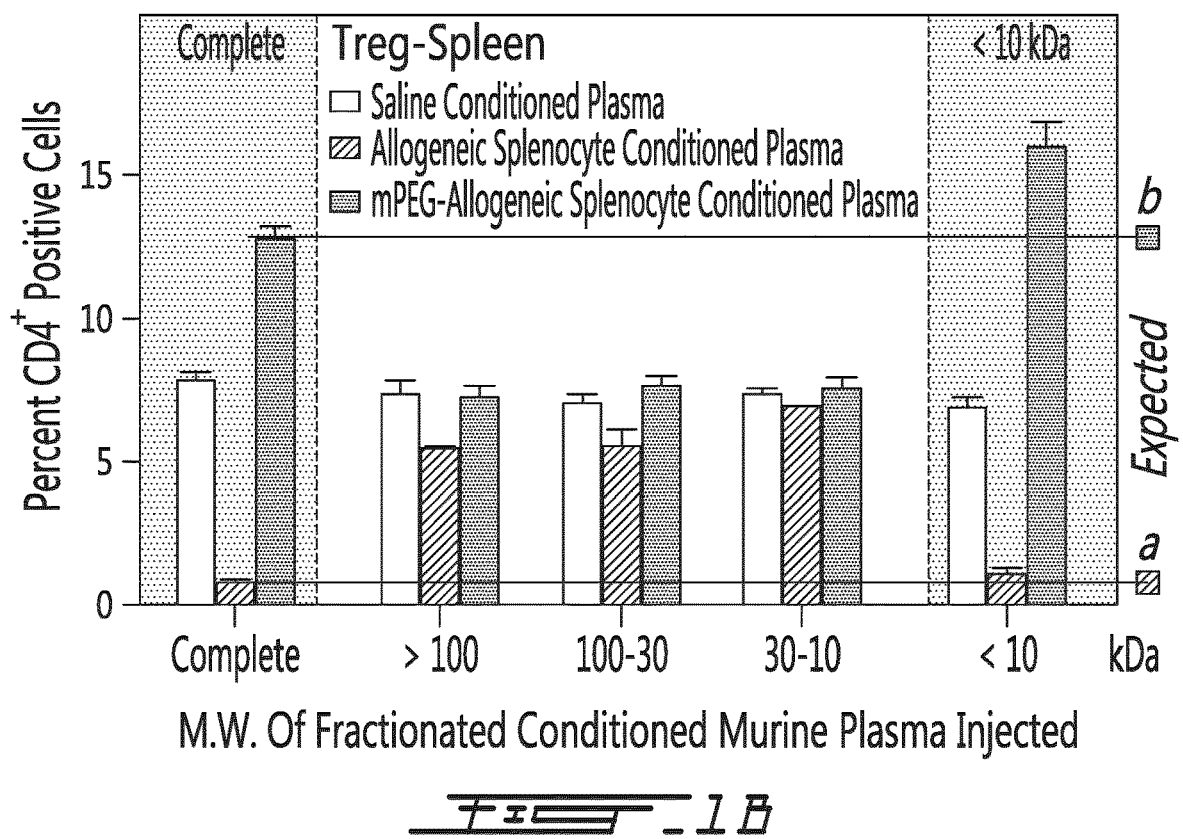
Figure 1C:
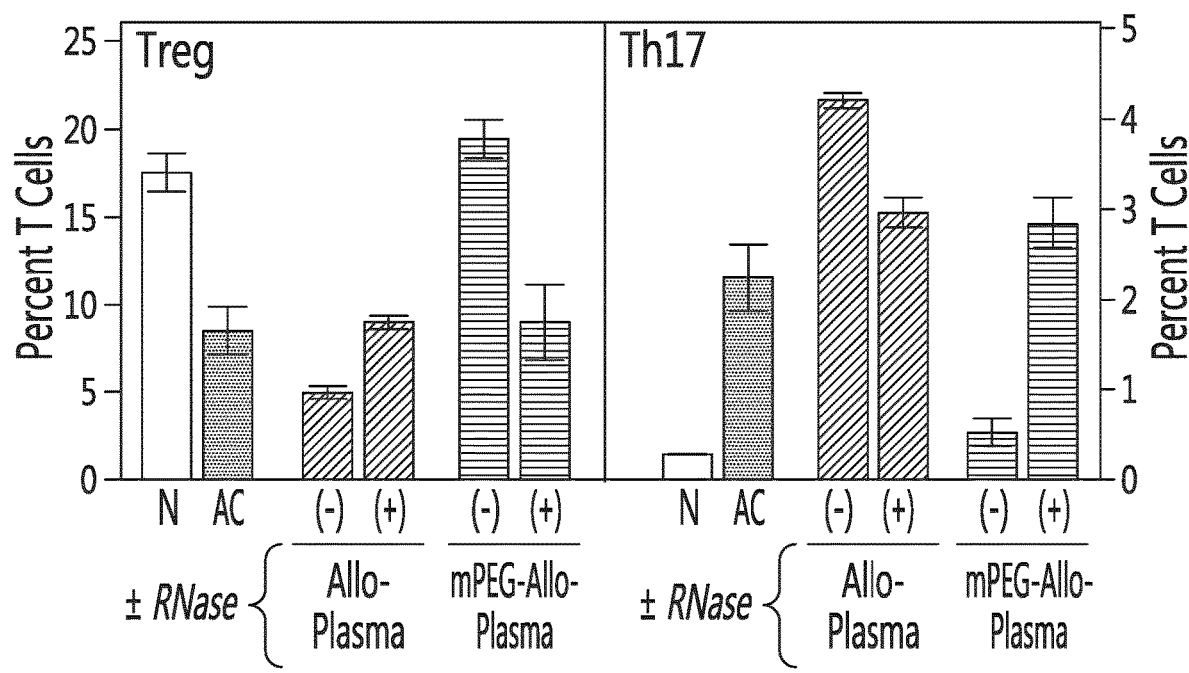

In a first series of experiment, several types of conditioned plasma were obtained. Briefly, the conditioned plasma was first obtained from Balb/c mice having received saline, $20 \times 10^6$ allogeneic (C57BL/6) PEGylated splenocytes (using 1 mM 20 kDa PEG) or $20 \times 10^6$ allogeneic (C57BL/6) unmodified splenocytes. The conditioned plasma was either left untreated (e.g. complete) or fractionated in function of the size of its components (>100 kDa, between 30 and 100 kDa, between 10 and 30 kDa or <10 kDa). The saline of the treated conditioned plasma was then transfused to naïve C57BL/6 mice. Five days after the administration, the animals were sacrificed, the spleen was obtained and the cells they contained was characterized. As shown on FIG. 1A, the <10 kDa fraction of the conditioned plasma from mouse having received unmodified allogeneic splenocytes retained the ability, when compared to complete unfractionated conditioned plasma, to increase Th17 levels in vivo. As shown on FIG. 1B, the <10 kDa fraction of the conditioned plasma from mouse having received unmodified allogeneic splenocytes retained the ability, when compared to complete unfractionated conditioned plasma, to decrease Treg levels in vivo. The immunodulatory effect of conditioned murine plasma seems to mostly reside in the lower molecular weight fraction (<10 kDa). This low molecular weight fraction does not include the majority of cytokines (usually encompasses in the 100-30 and the 30-10 kDa fractions) typically thought to mediate immunodulation of Tregs and pro-inflammatory leukocytes. However, the <10 kDa fraction is suspected to contain, among its components, microRNAs (miRNAs). To determine if the miRNAs in the conditioned plasma mediated the immunomodulatory effects observed with the conditioned plasma, mice were injected with untreated conditioned plasma or conditioned plasma that had been pre-treated with RNase A, an enzyme that degrades/destroys ribonucleic acids such as miRNAs. As noted in FIG. 1C, treatment with RNase A greatly reduced the immunomodulatory activity of the conditioned plasma, thereby confirming the ribonucleic acid nature of the size-fractionated conditioned plasma.

Figure 2A:
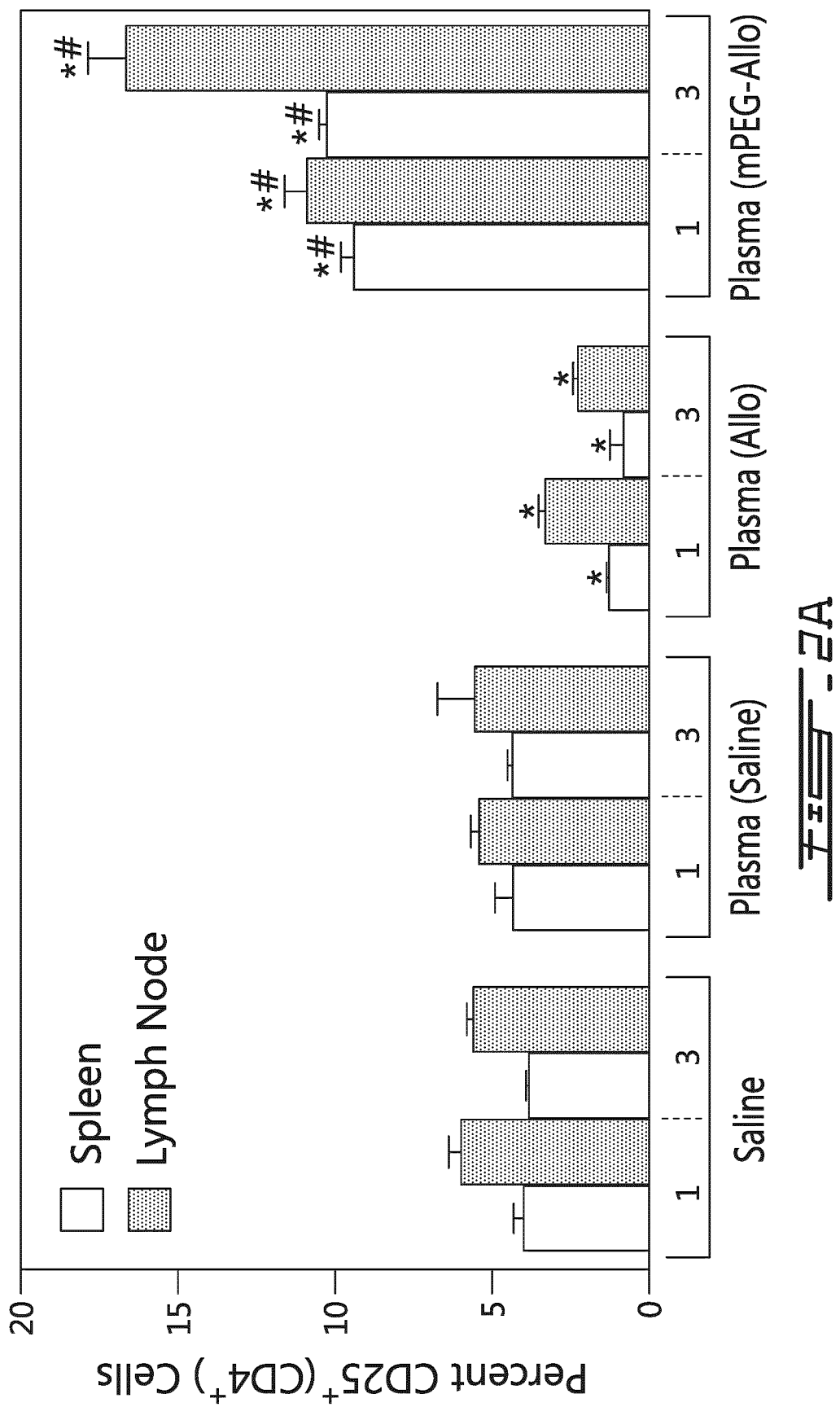
FIG. 2 illustrates the cellular modulation in Treg cells upon the administration of condition murine plasma. Saline, unmodified conditioned plasma (obtained by administering saline to the animal, identified as plasma(saline)), conditioned plasma obtained from the administration of non-modified allogeneic cells (identified as plasma (allo)) or the conditioned plasma obtained from the administration of polymer-modified allogeneic cells (identified as plasma (mPEG-Allo)) was injected once (1) or thrice (3) in the animals. After 5 days, the animals were sacrificed and their spleen and brachial lymph nodes were obtained. (A) Results are shown as the percentage of $CD4^+CD25^+$ T cells in function of type of conditioned plasma administered in the spleen (white bars) and in the brachial lymph nodes (black bars). * denotes p<0.001 relative to treatment with conditioned plasma from mice treated with saline, #denotes p<0.001 relative to treatment with conditioned medium derived from mice treated with unmodified allogeneic splenocytes. (B) Results are shown as the percentage of $CD69^+$ $CD4^+CD25^-$ T cells in function of type of conditioned plasma administered in the spleen (white bars) and in the brachial lymph nodes (black bars). * denotes p<0.001 relative to treatment with conditioned plasma from mice treated with saline, #denotes p<0.001 relative to treatment with conditioned medium derived from mice treated with unmodified allogeneic splenocytes. (C) Results are shown as the percentage of $Foxp3^+$, $CD25^+$ or $CD69^+$ of $CD4^+$ cells in function of the conditioned plasma administered in splenic cells (white bars) and lymph node cells (gray bars).

To determine the effects of acellular components obtained from administering non-polymer grafted (e.g., unmodified) allogeneic lymphocytes on the immune response, a second series of in vivo experiments was conducted. The conditioned plasma was first obtained from Balb/c mice having received saline, $20 \times 10^6$ allogeneic (C57BL/6) PEGylated splenocytes (using 1 mM 20 kDa PEG) or $20 \times 10^6$ allogeneic (C57BL/6) unmodified splenocytes. Saline or one of the conditioned plasma obtained was administered to Balb/c mice either once (at day 0) or thrice (at days 0, 2 and 4). Five days after the last administration, the animals were sacrificed, the spleen and the brachial lymph node were obtained and the cells they contained was characterized. More specifically, the percentage of $Foxp3^+$, $CD69^+$ or $CD25^+$ cells (with respect to the total number of $CD4^+$ recuperated) was determined. As shown in FIG. 2A, the number of $CD25^+$ cells was reduced in animals having received the conditioned plasma obtained from administering unmodified allogeneic splenocytes (Plasma (Allo) bars on FIG. 2A). On the other hand, the number of $CD25^+$ cells was elevated in animals having received the conditioned plasma obtained from administering PEGylated allogeneic splenocytes (Plasma (mPEG-Allo) bars on FIG. 2A). The population of $CD25^+$ cells include $Foxp3^+$ as well as $Foxp3^-$ Treg cells. These findings suggests that the conditioned plasma obtained from administering unmodified allogeneic splenocyte reduces Treg cell levels and induces a pro-inflammatory immune reaction.

Figure 2B:
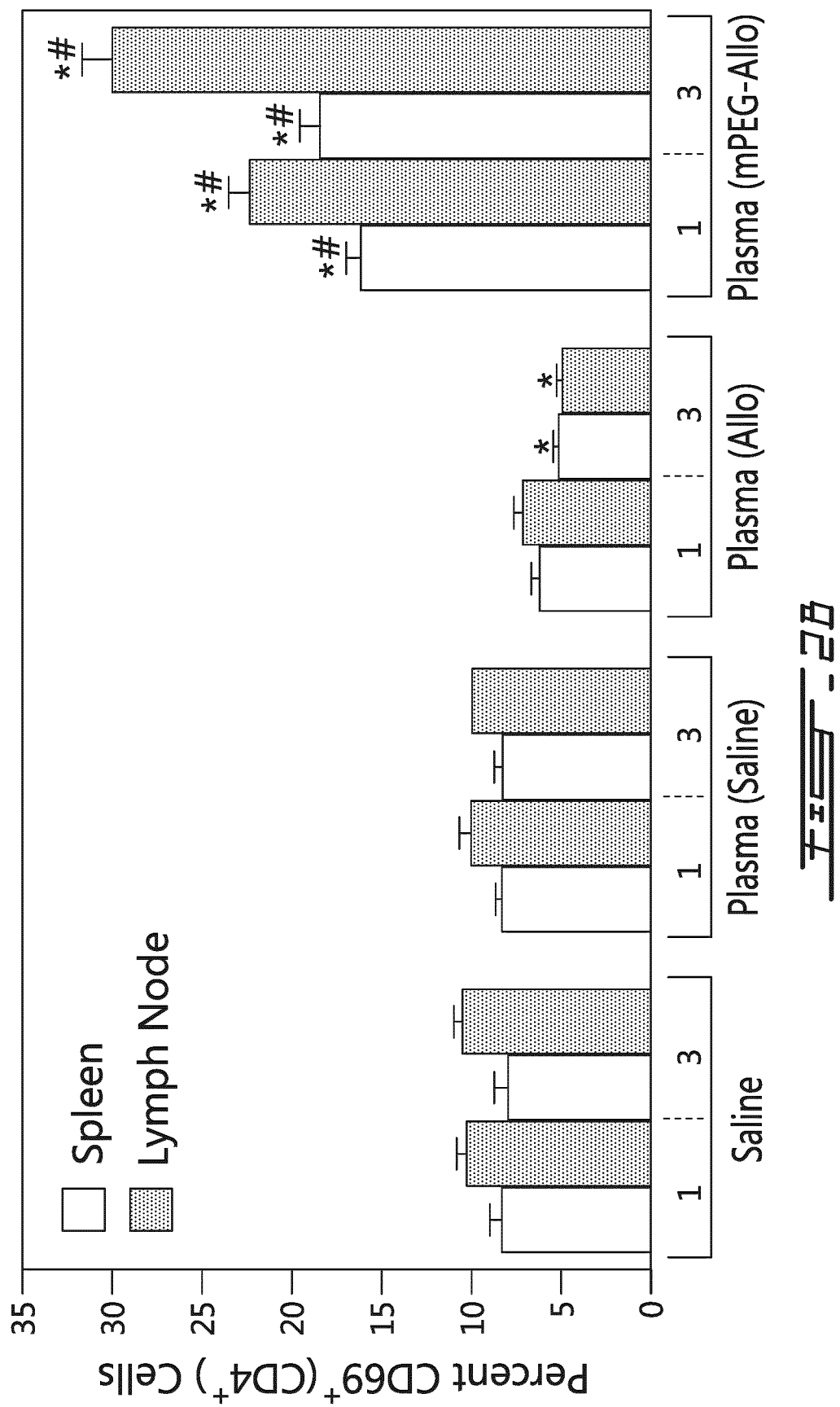
Figure 2C:
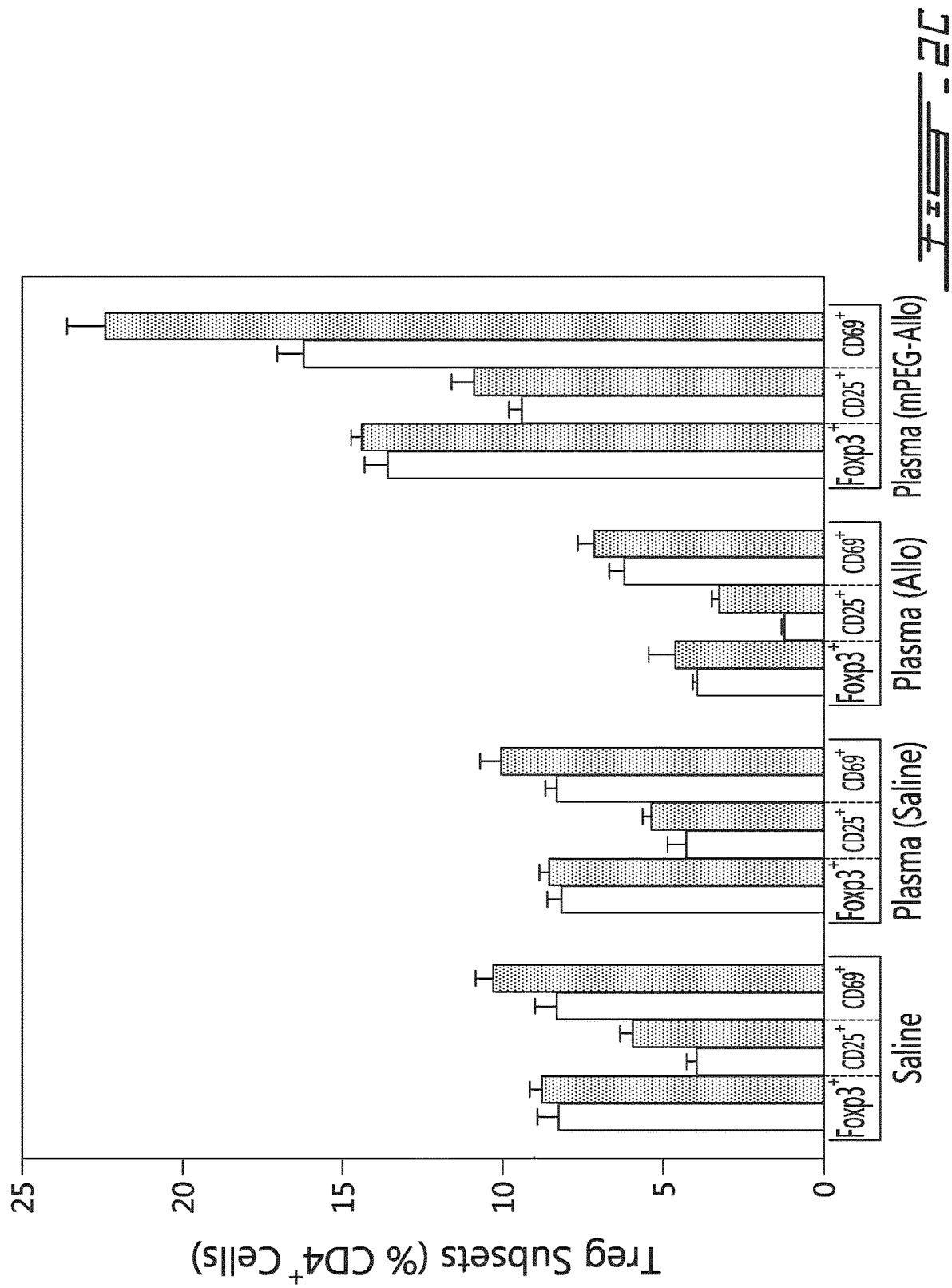

As shown in FIG. 2B, the number of $CD69^+CD25^-$ cells (e.g., non-Foxp3 Tregs) was reduced in animals having received the conditioned plasma obtained from administering unmodified allogeneic splenocytes (Plasma (Allo) bars on FIG. 2B). Non-Foxp3 Tregs are known to be elevated in tumor-bearing mouse models are believed to limit/prevent the tumor regression in these animals. These findings suggest that the conditioned plasma obtained from administering unmodified allogeneic splenocytes decreases the level of such Treg subset and may be beneficial in facilitating tumor regression in tumor-bearing animals.

Figure 3A:
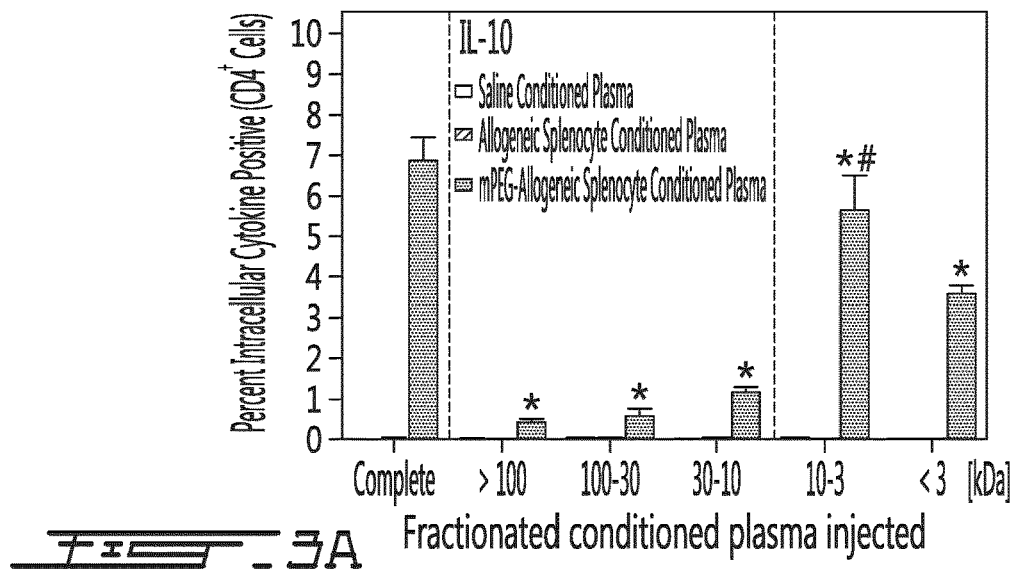
FIG. 3 illustrates the size fractionated conditioned plasma on the intracellular expression of cytokines. Unmodified conditioned murine plasma (obtained from donor mice 5 days post saline or splenocyte transfer), size fractionated-conditioned murine plasma was administered once to naïve mice and Treg/Th17 levels were measured (when) in the spleen. Results are shown as the percentage intracellular cytokine positive $CD4^+$ cells in function of type of conditioned medium (white bars=conditioned plasma obtained from administering saline, hatched bars=conditioned plasma obtained from administering unmodified allogeneic splenocytes, grey bars=conditioned plasma obtained from administering polymer modified allogeneic splenocytes) and size fractionation (non-fractioned or complete conditioned serum, fraction >100 kDa, fraction between 30 and 100 kDa, fraction between 10 and 30 kDa, fraction <10 kDa) for (A) IL-10, (B) IL-2, (C) IFN-γ, (D) TNF-α and (E) IL-4. * denotes p<0.001 relative to treatment with conditioned plasma from mice treated with saline, #denotes p<0.001 relative to treatment with conditioned medium derived from mice treated with unmodified allogeneic splenocytes.
Figure 3B:
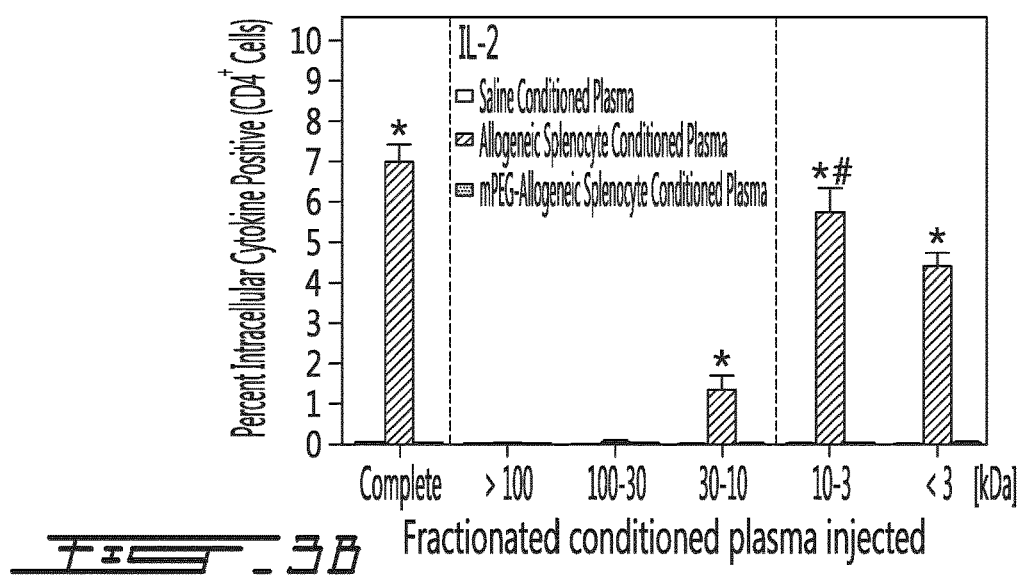
Figure 3C:
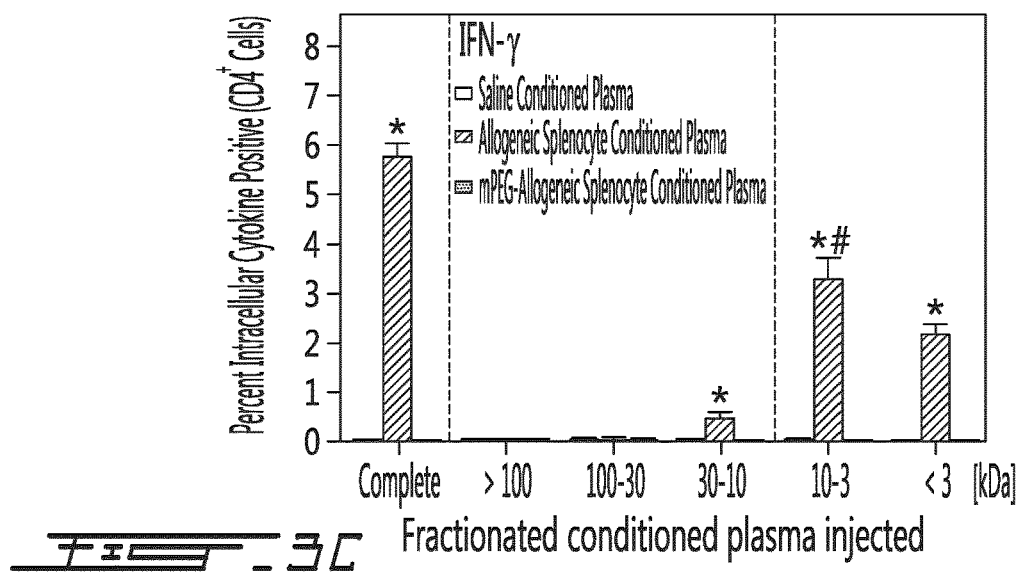
Figure 3D:
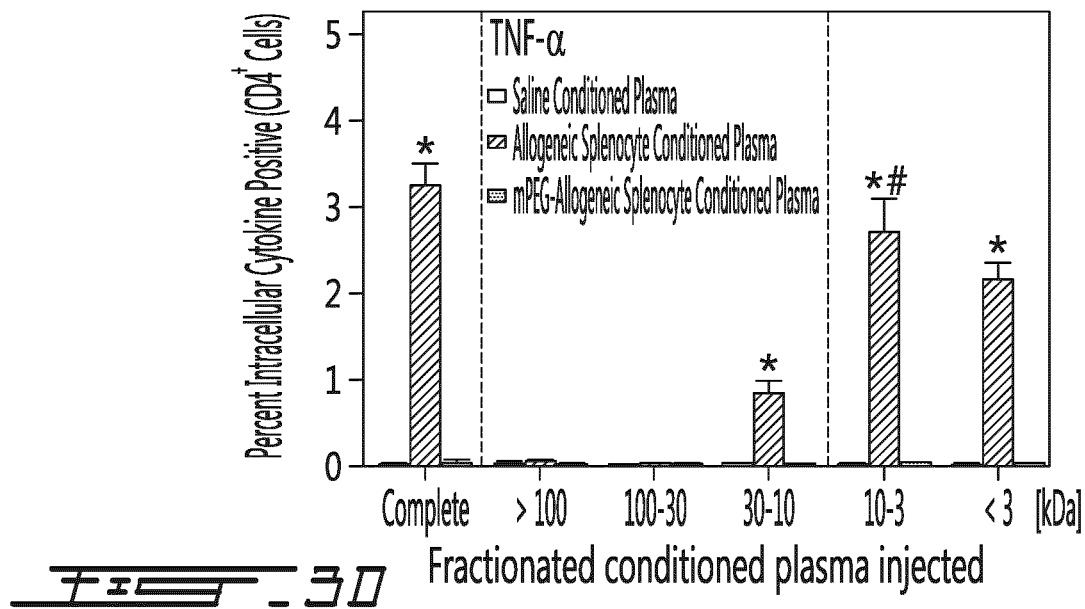
Figure 3E:
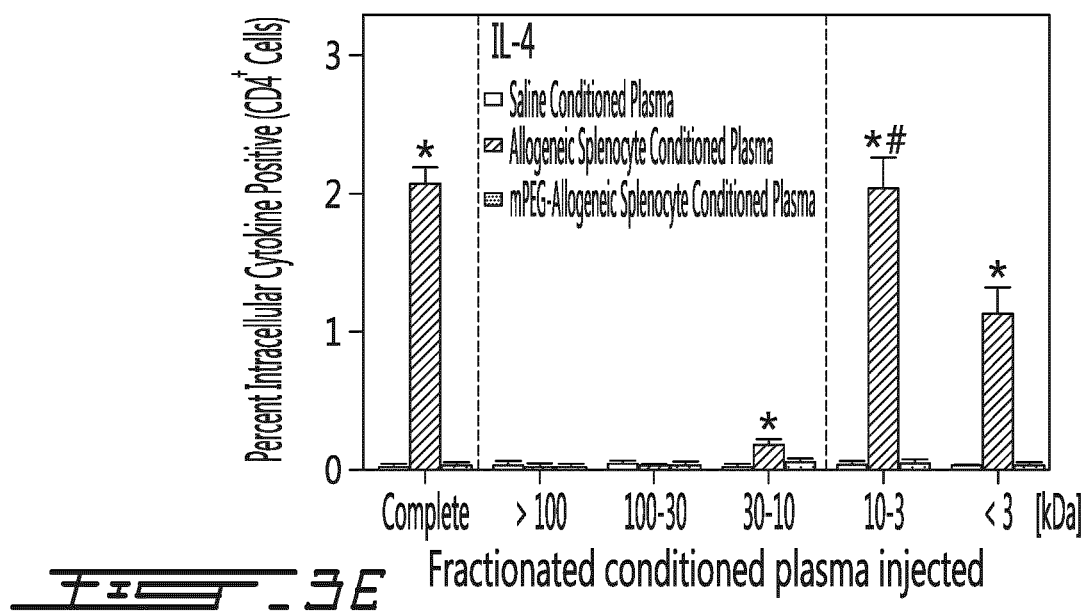

The size-fractionation conditioned plasma was administered to mice and its effects on the intracellular cytokine expression of $CD4^+$ cells was examined. As shown on FIG. 3, the <10 kDa fraction and some of the <3 kDa fraction of the conditioned plasma from mouse having received unmodified allogeneic splenotytes do not modulate IL-10 intracellular expression in $CD4^+$ cells in vivo (FIG. 3A). In contrast, the <10 kDa fraction and the <3 kDa fraction of the conditioned plasma from mouse having received unmodified allogeneic splenocytes increased IL-2, TNF-α, IFN-γ and IL-4 intracellular expression in $CD4^+$ cells in vivo (FIGS. 3B to 3E). The <10 kDa (and some of the >3 kDa) fraction of the conditioned plasma derived from unmodified allogeneic splenocytes, when compared to the corresponding fractions of the conditioned plasma derived from mPEG allogeneic splenocytes, increased the expression of pro-inflammatory cytokines, such as IL-2, TNF-α, IFN-γ or IL-4. However, pro-tolerogenic cytokines in animals having received conditioned plasma derived from unmodified allogeneic splenocytes remained at levels seen in naïve animals.

Example III

Characterization of miRNA Preparations Obtained with Non-Polymer Grafted Lymphocytes The material and methods used in this example are provided in Example I.

Figure 4C:
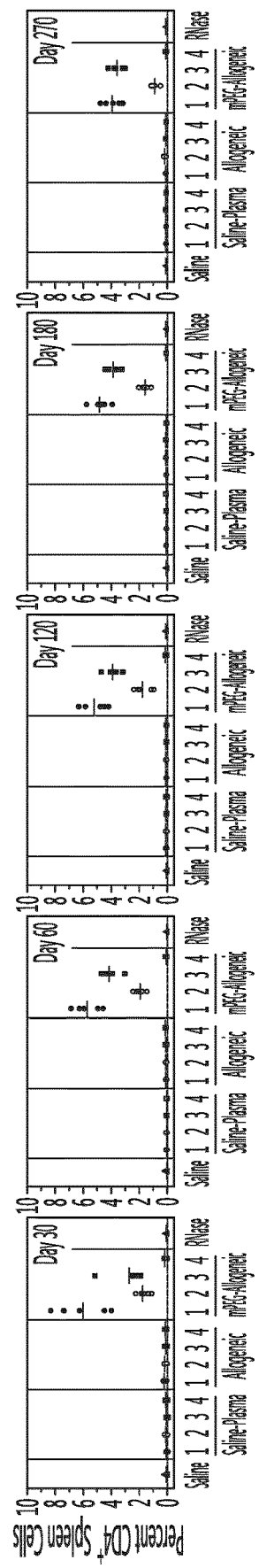
FIG. 4 illustrates the in vivo effects of the various conditioned medium and preparations derived therefrom on the intracellular expression of cytokines as well as type of $CD4^+$ cells. Conditioned plasma was obtained by administering naïve mice with saline, unmodified allogeneic splenocytes or polymer-modified allogeneic splenocytes (PEG) and recuperating plasma after 5 days. The obtained plasma was either administered directly (•=untreated) or optionally treated with RNaseA (○=conditioned plasma, ■=miRNA enriched fraction of conditioned plasma) and/or further purified so as to retain and enrich the <10 kDa fraction (e.g. miRNA) (■=untreated miRNA, □=RNase A-treated miRNA) prior to administration. As a control, RNase A was also administered directly to some animals. After 30, 60, 120, 180, 270 days, animals were sacrificed, their spleen was removed and $CD4^+$ cells were characterized by flow cytometry. Results are shown for intracellular cytokine expression: IL-2 (A), INF-γ (B), IL-10 (C), as well as $CD4^+$ cell type: Treg ($Foxp3^+$) (D) and Th17 ($IL-17^+$) (E) $CD4^+$ cells.

The conditioned plasma or the miRNA preparation (100 µL) obtained from the conditioned plasma (of mice having received saline, unmodified allogeneic splenocytes or polymer-modified allogeneic splenocytes) were administered intravenously to 7-8 week-old mice thrice (at days 0, 2 and 4). Cohorts (n=4) of mice were sacrificed at days 30, 60, 120, 180 and 270. Spleens were removed and $CD4^+$ cells were stained for intracellular expression of IL-2, IL-4, IL-10, INF-γ and TNF-α. Splenic Treg and Th17 populations were also measured. As shown on FIGS. 4A-C, the administration of the conditioned plasma or the derived miRNA preparation (i.e., IA1 preparations) from mouse having received unmodified allogeneic splenocytes caused an increase in the expression of intracellular IL-2 and INF-γ in $CD4^+$ cells. On the other hand, the administration of the conditioned plasma or the derived miRNA preparation from mouse having received mPEG-modified allogeneic splenocytes (i.e., TA1 preparation) caused an increase in the expression of intracellular IL-10 in $CD4^+$ cells. These modulations in expression were observed until at least 270 days after the administration of the conditioned medium or the miRNA preparation. This data suggests that miRNA was an active component mediating the immunological changes, RNase treatment of the conditioned plasma or of the miRNA preparation prior to administration to animals either diminished (plasma) or abolished (miRNA) the immunomodulatory effects. While conditioned plasma retained some immunomodulatory effect, it is believed that it was due to residual cytokines and/or plasma-mediated inactivation of the RNAase A enzyme.

Figure 4D:
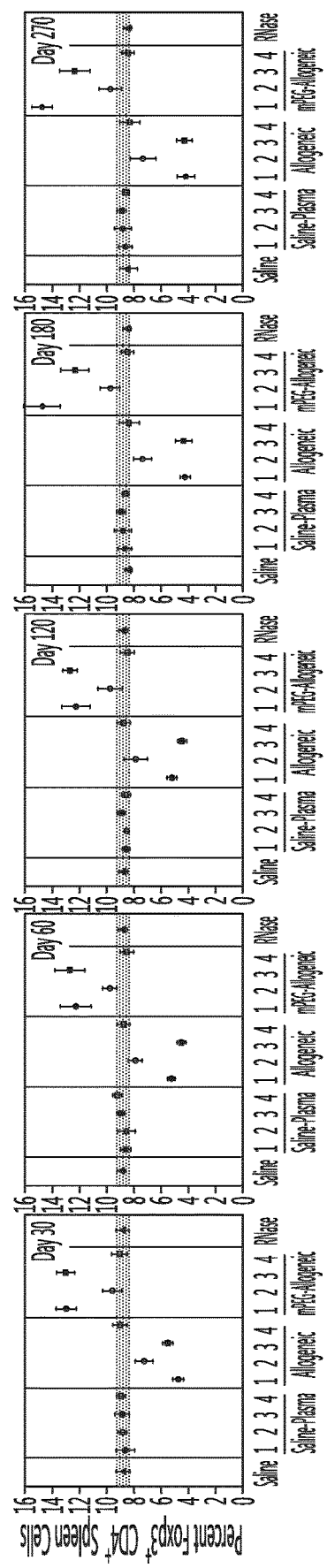
Figure 4E:
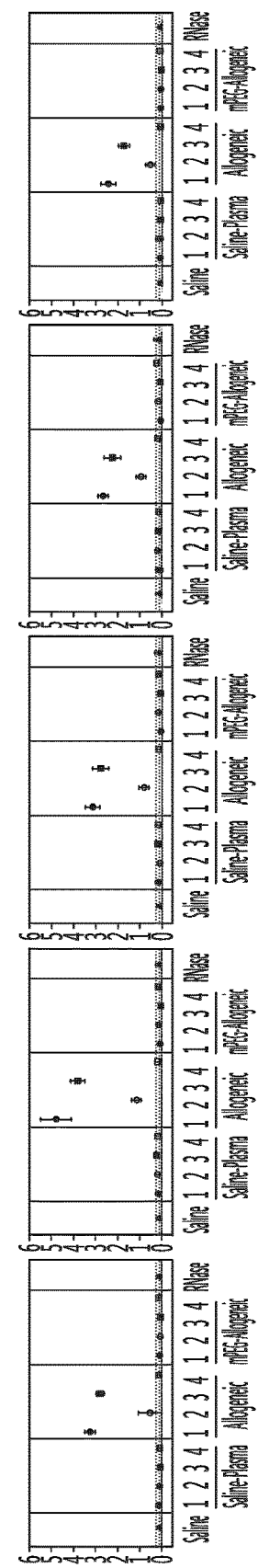

As also shown on FIG. 4D, the administration of the conditioned plasma or the derived miRNA preparation from mouse having received unmodified allogeneic splenocytes (i.e., IA1 preparations) caused a decrease in the percentage of Treg (Foxp3$^+$) cells in function of the total CD4$^+$ cells. In addition, the administration of the conditioned plasma or the derived miRNA preparation (i.e., IA1 preparations) from mouse having received unmodified allogeneic splenocytes caused an increase in the percentage of Th17 (IL-17$^+$) cells in function of the total CD4$^+$ cells (FIG. 4E). These modulations in CD4$^+$ cells types were observed at least 270 days after the administration of the conditioned medium or the miRNA preparations and were diminished (plasma) or abolished (miRNA) with a preliminary RNase treatment. Acellular preparations prepared from mice injected with either allogeneic leukocytes exerted potent and long-lasting effects in naive recipient mice. In aggregate, unmodified allogeneic-derived preparations (plasma or miRNA) yielded a pro-inflammatory state while mPEG-allogeneic-derived preparations (plasma or miRNA) yielded a immunoquiescent state.

Murine (IA1 preparations) miRNA preparations exert a direct effect on cell signaling. Murine IA1 preparations have been incubated with Jurkat cells (1×10$^6$ cells/ml treated with 50 µl of IA1/ml) and the level of phosphorylation of some of the phosphokinase has been measured after 30 minutes of incubation. As shown on FIG. 5, IA1 preparations favored the phosphorylation of the HSP60 and WNK1 kinases.

Figure 6:
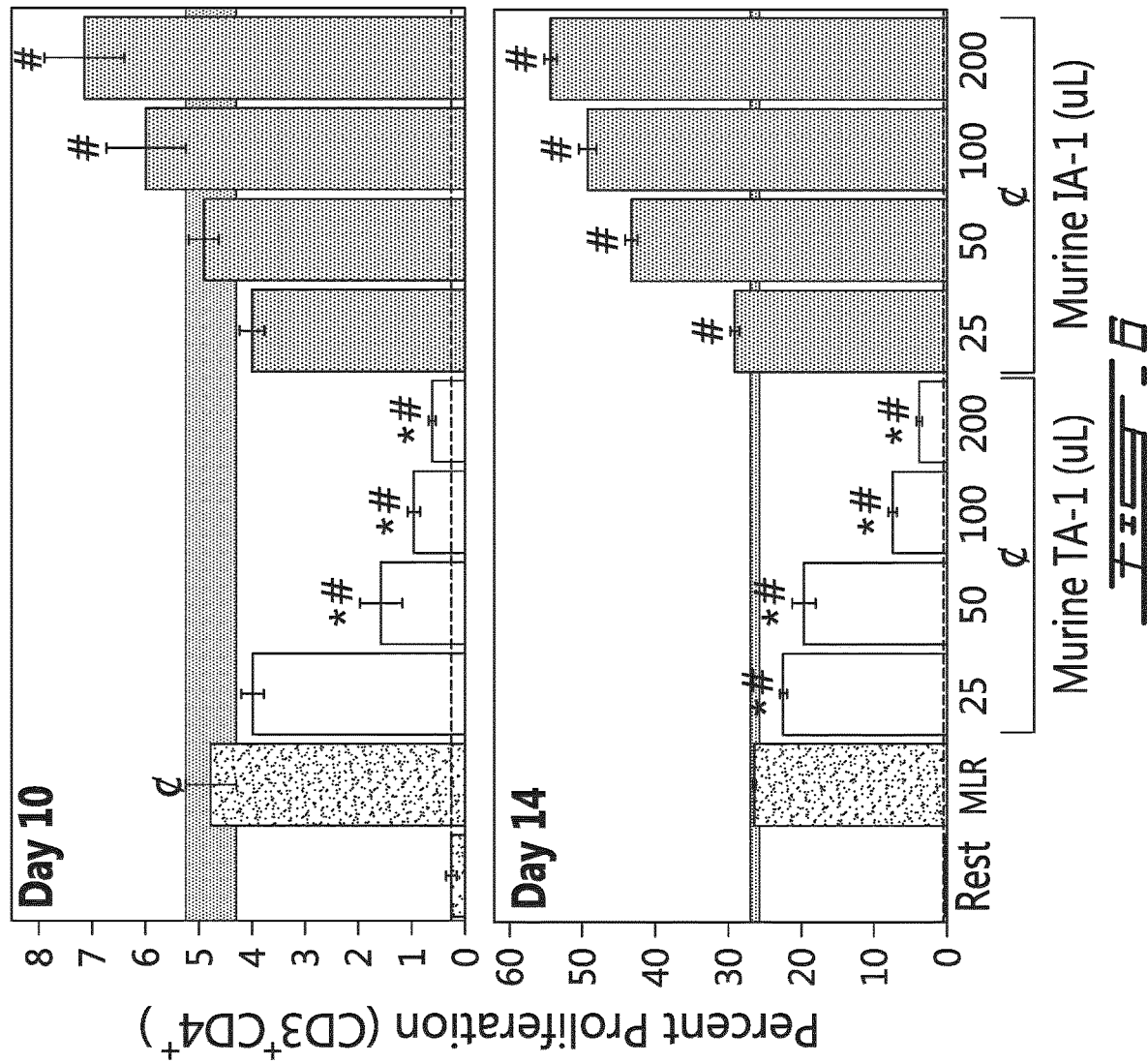
FIG. 6 illustrates the in vitro effects of the murine IA1 preparations on human PBMCs. Murine TA1 or IA1 preparations (either 25 μL, 50 μL, 100 μL or 200 μL) were included in a human PBMC MLR assay and cellular proliferation was measured. Results are shown as percent in proliferation ($CD3^+CD4^+$ cells) in function of conditions (Rest=resting MLR, MLR=conventional MLR without TA1, Murine TA-1=MLR with TA1, Murine IA-1=MLR with IA1) and TA1/IA1 concentration (in μL) after 10 days (A) or 14 days (B). #denotes p<0.001 relative to conventional MLR value and * denotes p<0.001 relative to murine IA1 MLR. ¢ denotes the concentration of the TA1 or IA1 preparation used in the in vivo mouse study (e.g., FIG. 7).

Murine IA1 preparations were also introduced (at time 0) into a human PBMC MLR assay in order to determine their effect on human allo-recognition. As indicated on FIG. 6, the presence of the murine IA1 preparations resulted in a dose-dependent increase in the percentage in leukocyte proliferation (at both 10 and 14 days) which is indicative of their pro-inflammatory effects. This data also indicates that the IA1 preparations show significant evolutionary conservations (both sequence specific and similarity) since the murine IA1 preparations are highly effective in a xenogeneic system (e.g. human MLR).

Figure 7:
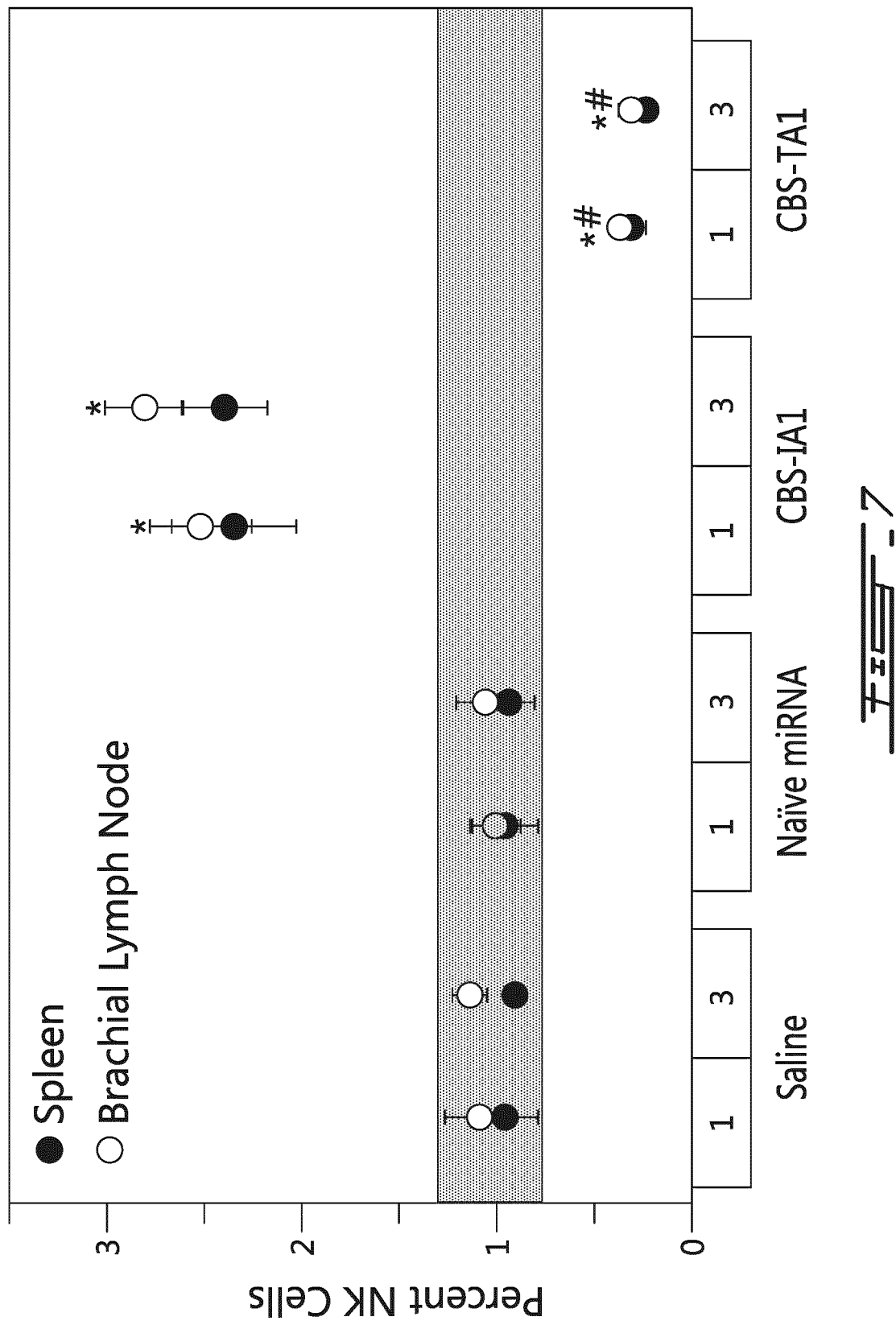
FIG. 7 illustrates the in vivo effects of the murine IA1 preparations on NK cells. Saline, miRNA preparations obtained from naïve animals, AI1 or TA1 preparations were administered once (1) or thrice (3) in naïve animals. Five days after the last administration, the mice were sacrificed, their spleen and brachial lymph nodes obtained and the cells they contained was characterized. Results are shown as the percentage of NK cells (with respect to the total number of $CD4^+$ cells) in function of treatment in the spleen (•) and the brachial lymph nodes (○).* denotes p<0.001 relative to saline and #denotes p<0.001 relative to murine IA1 preparations.

Murine IA1 or TA1 preparations (100 µL) were administered once (at day 0) or thrice (at days 0, 2 and 4). Five days after the last administration, the mice were sacrificed, their spleen and brachial lymph nodes were obtained and the cells they contained were characterized. As seen in FIG. 7, IA1 preparations, unlike TA1 preparations, increased the percentage of NK cells (as measured by flow cytometry) with respect to the total number of CD4$^+$ cells. Similar results were obtained in the spleen and the lymph nodes. As it is known in the art, NK cells can play a crucial role in tumor destruction. As murine IA1 preparations are capable of inducing a potent increase in NK cells, they can be used to facilitate tumor regression in tumor-bearing animals.

Example IV miRNA Characterization of Acellular Protolerogenic Preparations

Some of the material and methods referred to in this example are provided in Example I.

In order to characterize the constituents of the miRNA preparations, the miRNA of conditioned medium collected at 72 hours from resting human PBMC, a human control MLR (using two HLA disparate PBMC populations), and a mPEG MLR (using the same two allogeneic PBMC populations wherein one population is modified with a polymer, e.g. mPEG) and compared via qPCR analysis. The miRNA preparations obtained from the human control MLR is referred to as IA2. The miRNA preparations obtained from the human mPEG MLR is referred to TA2. The combined average of the resting Donor A and resting Donor B (i.e., resting AB) were used, unless otherwise noted, for baseline in all analyses.

As shown in FIG. 8A, when the IA2 miRNA population is compared to the miRNA population of the supernatant of resting cells, using a volcano plot analysis, at least five different miRNAs are differentially expressed (e.g. increased) by statistical significance ($p<0.01$ for miR-9-5p, miR-155-5p, miR-206, miR-147a and $p<0.05$ for miR-214-3p) and at least one miRNA is modulated by at least a $\log_2$ (e.g. miR-302a-3p).

In contrast, as shown in FIG. 8B, when the TA2 miRNA population is compared, using a volcano plot analysis, with the miRNA population of the supernatant of resting cells, at least one miRNA is differentially expressed (e.g. increased) by statistical significance ($p<0.05$ for miR-214-3p) and at least one miRNA is modulated by at least a $\log_2$ fold (e.g. miR-149-5p).

A direct comparison of TA2 miRNA population to IA2 miRNA populations as shown in FIG. 8C, demonstrates that at least two miRNAs are differentially expressed by volcano statistical significance ($p<0.01$ for miR-155-5p and $p<0.05$ for miR-9-5p) and at least two miRNAs are modulated by at least a $\log_2$ (e.g. miR-183-5p and mir-147a).

On FIG. 8C, nine miRNA species were identified. These miRNA species were selected because they were considered to be differentially expressed as determined by clustergram analysis between the AI2 and TA2 preparations. The miRNA species identified with 1, 2, 3, 5, 6, 8 and 9 showed increased abundance in the TA2 preparations relative to the IA2 preparations. The miRNA species identified with 4 has a relative abundance similar in both the IA2 preparation and TA2 preparations and elevated relative to resting cells.

Further characterization of the miRNA population of the IA2 preparations and the TA2 preparations is provided in fold change analysis. FIG. 9 provides a summary of the fold regulation of the purified miRNA preparations differentially expressed in the IA2 preparations and the TA2 preparations when compared to the conditioned medium of resting cells.

FIG. 10 provides a subset of the miRNAs presented in FIG. 9 and exhibiting at least a $\log_2$ fold modulation when compared to resting cells. As indicated in FIG. 10, a subpopulation of miRNAs are decreased in the TA2 preparations and increased in the IA2 preparations (miR-183-5p, miR-203a, miR363-3p). As also indicated in FIG. 10, another subpopulation of miRNAs are increased in the TA2 preparation and decreased in the AI2 preparations (miR-21-5p, miR-27a-3p, miR 27b-3p, miR-298, miR-34a-5p, let-7a-5p, let-7e-5p, miR-132-3p).

REFERENCES

Chen A M, Scott M D. Immunocamouflage: prevention of transfusion-induced graft-versus-host disease via polymer grafting of donor cells. J Biomed Mater Res A 2003; 67:626-36.

Chen A M, Scott M D. Comparative analysis of polymer and linker chemistries on the efficacy of immunocamouflage of murine leukocytes. Artif Cells Blood Substit Immobil Biotechnol 2006; 34:305-22.

Murad K L, Gosselin E J, Eaton J W, Scott M D. Stealth cells: prevention of major histocompatibility complex class II-mediated T-cell activation by cell surface modification. Blood 1999; 94:2135-41.

O'Neill D W, Bhardwaj N. Differentiation of peripheral blood monocytes into dendritic cells. Curr Protoc Immunol; 2005. Chapter 22: Unit 22F.4.

Scott M D, Murad K L, Koumpouras F, Talbot M, Eaton J W. Chemical camouflage of antigenic determinants: stealth erythrocytes. Proc Natl Acad Sci USA 1997; 94:7566-71.

Wang D, Toyofuku W M, Chen A M, Scott M D. Induction of immunotolerance via mPEG grafting to allogeneic leukocytes. Biomaterials. 2011 December; 32(35):9494-503.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A process for making an acellular pro-inflammatory preparation and decreasing a ratio of endogenous regulatory T (Treg) cell concentration to endogenous pro-inflammatory T cell concentration in a subject, said process comprising:
   (i) contacting a first leukocyte with a second leukocyte in vitro under conditions to allow a pro-inflammatory allo-recognition to provide a conditioned preparation, wherein the first leukocyte is allogeneic to the second leukocyte;
   (ii) separating whole first leukocyte cells and whole second leukocyte cells from the conditioned preparation to obtain an acellular conditioned preparation;
   (iii) selecting miRNA components having an individual average molecular weight of less than about 10 kDa from the acellular conditioned preparation under conditions to inhibit RNA degradation and to maintain a relative abundance of each of the miRNA components so as to obtain a composition enriched in acellular pro-inflammatory components;
   (iv) formulating the composition of step (iii), under conditions to inhibit RNA degradation and to maintain a relative abundance of each of the miRNA components, in the acellular pro-inflammatory preparation for administration to the subject, and
   (v) administering a therapeutically effective amount of the acellular pro-inflammatory preparation to the subject, wherein the acellular pro-inflammatory preparation, when administered to the subject, decreases the ratio of endogenous regulatory T (Treg) cell concentration to endogenous pro-inflammatory T cell concentration in the subject.

2. The process of claim 1, comprising culturing the first leukocyte and the second leukocyte.

3. The process of claim 2, wherein the conditioned preparation is a supernatant of the cell culture.

4. The process of claim 1, further comprising, prior to step (i), preventing one of the first leukocyte or the second leukocyte from proliferating.

5. The process of claim 1, wherein step (ii) further comprises filtering out components having the average molecular weight of more than about 10 kDa from the conditioned preparation.

6. The process of claim 1, wherein step (iv) further comprises formulating the composition for intravenous administration to the subject.

7. The process of claim 1, wherein at least one of the first leukocyte and the second leukocyte is a T cell.

8. The process of claim 7, wherein the T cell is a CD4-positive T cell.

9. The process of claim 7, wherein the T cell is a CD8-positive T cell.

10. The process of claim 1, wherein at least one of the first leukocyte and the second leukocyte is a peripheral blood mononucleated cell.

11. The process of claim 1, wherein at least one of the first leukocyte and the second leukocyte is a splenocyte.

12. The process of claim 1, wherein the subject has a condition caused or exacerbated by a reduced immune response in the subject.

13. The process of claim 12, wherein the condition is a proliferation-associated disorder.

14. The process of claim 13, wherein the proliferation-associated disorder is cancer.

15. The process of claim 12, wherein the condition is an infection.

16. The process of claim 15, wherein the infection is selected from the group consisting of a parasitic infection, a viral infection, a bacterial infection, and a fungal infection.

17. The process of claim 1, wherein the subject has a malignant tumor and the acellular pro-inflammatory preparation, when administered to the subject, limits the growth of the malignant tumor.

18. The process of claim 1, wherein the subject has a malignant tumor and the acellular pro-inflammatory preparation, when administered to the subject, reduces the size of the malignant tumor.

* * * * *